(12) United States Patent
Kostic et al.

(10) Patent No.: US 10,231,647 B2
(45) Date of Patent: Mar. 19, 2019

(54) PERSON SUPPORT APPARATUS WITH POSITION MONITORING

(71) Applicant: Stryker Corporation, Kalamazoo, MI (US)

(72) Inventors: Marko N. Kostic, Portage, MI (US); Jonathan Mark Greenbank, Plainwell, MI (US); Christopher J. Cummings, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/793,599

(22) Filed: Oct. 25, 2017

(65) Prior Publication Data

US 2018/0055418 A1 Mar. 1, 2018

Related U.S. Application Data

(63) Continuation of application No. 14/692,871, filed on Apr. 22, 2015, now Pat. No. 9,814,410.

(Continued)

(51) Int. Cl.
*A61B 5/11* (2006.01)
*G01J 5/00* (2006.01)
(Continued)

(52) U.S. Cl.
CPC .............. *A61B 5/11* (2013.01); *A61G 7/05* (2013.01); *A61G 7/0527* (2016.11); *A61G 7/0528* (2016.11); *A61G 13/10* (2013.01); *G01D 5/40* (2013.01); *G01G 19/44* (2013.01); *G01G 19/445* (2013.01); *G01J 5/00* (2013.01); *G01J 5/0025* (2013.01); *G01J 5/12* (2013.01); *G01J 5/14* (2013.01); *A61B 5/1115* (2013.01); *A61G 5/101* (2013.01); *G01J 2005/0077* (2013.01); *G01J 2005/123* (2013.01)

(58) Field of Classification Search
CPC ....... A61G 7/0527; A61G 7/0528; A61B 5/11
See application file for complete search history.

(56) References Cited

U.S. PATENT DOCUMENTS 5,276,432 A 1/1994 Travis
5,742,055 A 4/1998 Lee
(Continued)

FOREIGN PATENT DOCUMENTS

WO 2011113070 A1 9/2011
WO 2012122002 A1 9/2012

*Primary Examiner* — Hugh H Maupin
(74) *Attorney, Agent, or Firm* — Warner Norcross + Judd LLP

(57) ABSTRACT

A person support apparatus includes one or more thermal image sensors whose outputs are analyzed to perform one or more functions. Such functions include automatically turning on a brake, automatically turning on one or more lights, detecting when a patient associated with the person support apparatus has fallen, enabling a propulsion system of the patient support apparatus to be used, automatically controlling one or more environmental controls, and/or automatically arming an exit detection system after entry of a patient onto the person support apparatus. Multiple thermal images may be generated from multiple sensors to generate stereoscopic thermal images of portions of the person support apparatus and its surroundings.

18 Claims, 15 Drawing Sheets

Related U.S. Application Data

(60) Provisional application No. 61/989,243, filed on May 6, 2014.

(51) Int. Cl.
    *A61G 7/05*         (2006.01)
    *A61G 13/10*       (2006.01)
    *G01D 5/40*        (2006.01)
    *G01G 19/44*       (2006.01)
    *G01J 5/14*        (2006.01)
    *G01J 5/12*        (2006.01)
    *A61G 5/10*        (2006.01)

(56) References Cited

U.S. PATENT DOCUMENTS

| | | |
|---|---|---|
| 6,791,460 B2 | 9/2004 | Dixon et al. |
| 7,690,059 B2 | 4/2010 | Lemire et al. |
| 7,985,953 B2 | 7/2011 | Luterotti et al. |
| 8,350,709 B2 | 1/2013 | Receveur |
| 8,514,280 B2 | 8/2013 | Zisa et al. |
| 8,620,625 B2 | 12/2013 | Sing et al. |
| 8,907,287 B2 | 12/2014 | Vanderpohl |
| 2005/0077469 A1 | 4/2005 | Kaushal |
| 2007/0163045 A1 | 7/2007 | Becker et al. |
| 2008/0021344 A1 | 1/2008 | Jung et al. |
| 2011/0241886 A1 | 10/2011 | Receveur |
| 2012/0025991 A1* | 2/2012 | O'Keefe ............... A61B 5/1115 340/573.4 |
| 2012/0075464 A1 | 3/2012 | Derenne et al. |
| 2013/0076517 A1 | 3/2013 | Penninger et al. |
| 2014/0265502 A1 | 9/2014 | Hough et al. |
| 2014/0276671 A1 | 9/2014 | Gooding |
| 2015/0112151 A1 | 4/2015 | Muhsin et al. |

\* cited by examiner

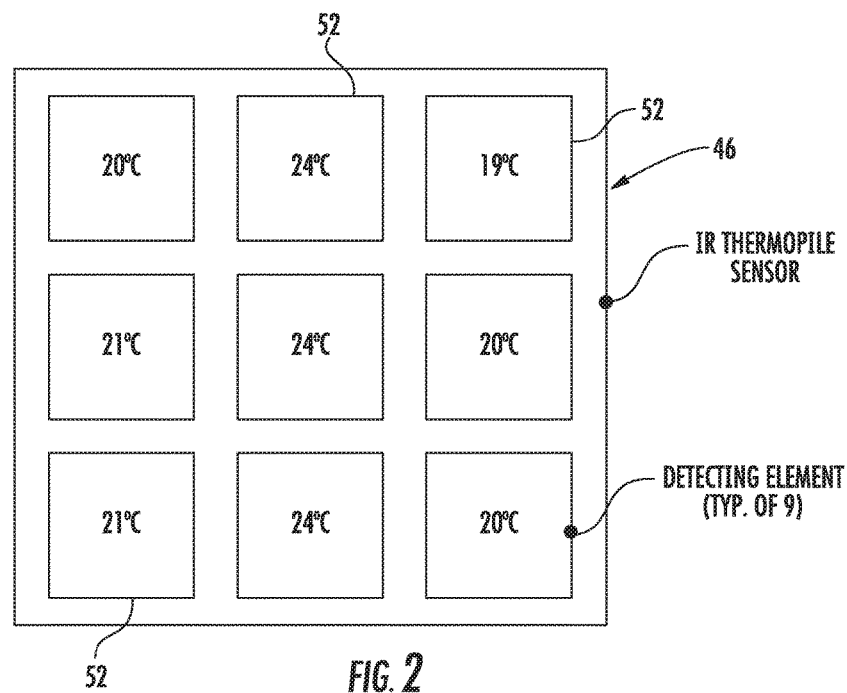
FIG. 2
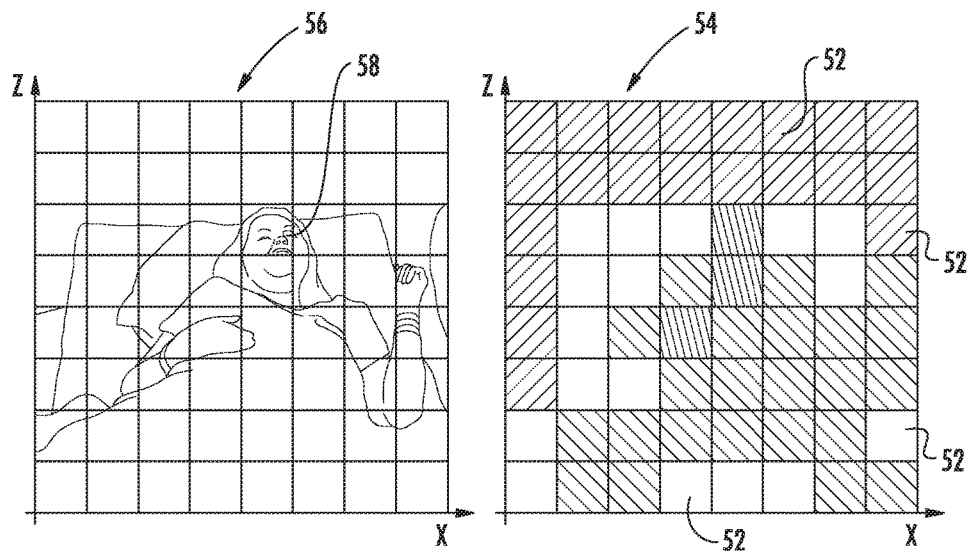
FIG. 3A
FIG. 3B

BRAKE-ENABLE SYSTEM

AUTO DISPLAY AND LIGHTING CONTROL

FALLEN PATIENT DETECTION DIAGRAM

PROPULSION SYSTEM ENABLE

ENVIRONMENTAL CONTROLS (HVAC) - BED MICROENVIRONMENT CONTROL

PERSON SUPPORT APPARATUS WITH POSITION MONITORING

CROSS-REFERENCE TO RELATED APPLICATIONS

This application is a continuation of U.S. patent application Ser. No. 14/692,871 filed Apr. 22, 2015, by inventors Marko Kostic et al. and entitled PERSON SUPPORT APPARATUS WITH POSITION MONITORING, which in turn claims priority to U.S. provisional patent application Ser. No. 61/989,243 filed May 6, 2014 by inventors Marko N. Kostic et al. and entitled PERSON SUPPORT APPARATUS WITH POSITION MONITORING, the complete disclosures of both of which are hereby incorporated herein by reference.

BACKGROUND

The present disclosure relates to person support apparatuses such as, but not limited to, beds, stretchers, cots, recliners, wheelchairs, operating tables, and the like.

SUMMARY

Various person support apparatuses are disclosed herein that operate in conjunction with one or more position monitors in order to carry out one or more functions that are at least partially based upon the output of the position monitor. In some embodiments, the position monitor includes one or more infrared sensors that are adapted to generate a thermal image of objects and/or persons. In some embodiments, the position monitor is used to carry out one or more of the following functions: determining whether a person is present on the person support apparatus; determining whether the person may be about to exit the person support apparatus; determining an orientation of a person on the person support apparatus; changing an illumination intensity of a display supported on the person support apparatus; determining whether to change a state of a brake of the person support apparatus; enabling or disabling a user input of the person support apparatus; adjusting a heating, ventilation, and air conditioning (HVAC) system; and/or determining whether a person has fallen.

In one embodiment, a person support apparatus is provided that includes a support surface, first and second sensors, and a controller. The first sensor is adapted to detect electromagnetic waves coming from the person when the person is supported on the support surface. The second sensor is adapted to detect a force exerted by the person while the person is supported on the support surface. The controller is adapted to correlate information from the first and second sensors in order to determine a position of the person on the support surface.

According to another embodiment, a person support apparatus is provided that includes a support surface, a sensor, and a controller. The sensor is adapted to detect the presence of the person when the person is not positioned on the support surface but within a vicinity of the person support apparatus. The controller is adapted to automatically carry out at least one of the following functions in response to detecting the presence of the person: (1) change an illumination intensity of a display supported on the person support apparatus, (2) determine whether to change a state of a brake of the person support apparatus; (3) enable a user input of the person support apparatus; and (4) determine if the person has fallen.

According to yet another embodiment, a person support apparatus is provided that includes a support surface, first and second sensors, and a controller. The first sensor and second sensors are both adapted to detect electromagnetic waves coming from an entity when the entity is supported on the support surface. The first sensor is positioned at a first location on the person support apparatus, and the second sensor is positioned at a second location on the person support apparatus that is spaced from the first location by a known distance. The controller is adapted to determine a distance between a reference location on the entity and one or both of the first and second sensors based upon the known distance and information received from the first and second sensors.

According to still another embodiment, a person support apparatus is provided that includes a support surface, a sensor, and a controller. The sensor is adapted to generate a thermal image, or a map, of a person when the person is supported on the support surface. The controller is adapted to analyze the thermal image to distinguish between a first portion of the thermal image corresponding to the person and a second portion of the thermal image corresponding to the person's surroundings. The controller is further adapted to distinguish between the first and second portions without utilizing any markers placed on the person that have predefined thermally identifiable characteristics.

According to other aspects, the first sensor and/or second sensor may be infrared sensors. In other embodiments, the first sensor is an infrared sensor and the second sensor is adapted to detect a force exerted by the person while supported on the support surface. When the second sensor is implemented as a force sensor, it may comprise a plurality of load cells that are adapted to detect a weight of the person when the person is positioned on the support surface.

A user input may be included that is adapted to arm and disarm a person monitor. The controller is adapted to issue an alert if the person monitor is armed and the position of the person on the support surface changes by more than a predetermined threshold.

The controller may determine the existence of any one of more of the following conditions based on any one or more of the sensor outputs: a person is sitting up on the support surface; a person is lying on his or her back on the support surface; a person is lying on his or her side on the support surface; a person's legs have moved beyond an edge of the support surface; a person has turned from his or her back to his or her side on the support surface, or vice versa; a person is standing next to the person support apparatus; and a person is standing adjacent one or more user controls on the person support apparatus that are adapted to control motorized propulsion of the person support apparatus.

In any of the embodiments, the controller may be further adapted to determine a three-dimensional position of the person on the support surface. The person support apparatus may additionally include a wheel and a brake for the wheel, wherein the controller is adapted to automatically change the brake to a braked state based at least partially upon the information from either or both of the first and second sensors. In one embodiment, the controller automatically activates the brake if the detected person subsequently leaves the vicinity of the person support apparatus without having manually activated the brake.

The person support apparatus may also include a plurality of side rails, a footboard, and a headboard, wherein at least one of the sensors is positioned on one of the side rails, footboard, and headboard.

In still other embodiments, the controller is further adapted to determine if a blanket is positioned on top of the person. The controller may further be adapted to issue an alert if the blanket is moved off the person without the person sitting up, or if the person is determined to be asleep while the blanket is moved off the person.

The support apparatus may be configured to automatically illuminate the display when the presence of a person is detected, particularly the presence of a person who is positioned off of the person support apparatus. When so configured, the person support apparatus may further include an ambient light sensor in communication with the controller, wherein the controller changes the illumination intensity of the display based upon a signal from the ambient light sensor. The display may be mounted to the footboard, or to other locations on the person support apparatus.

In some embodiments, a first infrared sensor is provided that is adapted to detect first infrared waves emanating from the person that are above a threshold height and a second infrared sensor is provided that is adapted to detect second infrared waves emanating from the person that are below the threshold height. The controller determines if a person has fallen based upon a comparison of the first infrared waves and the second infrared waves.

In some embodiments, first and second sensors are provided that are both adapted to produce thermal images of the person and the controller is adapted to generate a stereoscopic thermal image by combining the thermal images from the first and second sensors.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 2 is a diagram of an illustrative 3×3 thermopile sensor that may be used with any of the person support apparatuses disclosed herein;

FIG. 3A is an arbitrary example of a visual image of a person supported on one of the person support apparatuses, as would be captured by an 8×8 visual sensor;

FIG. 3B is a diagram of an illustrative 8×8 thermopile sensor that may be used with any of the person support apparatuses disclosed herein, and includes a thermal image generally corresponding to the visual image of FIG. 3A;

DETAILED DESCRIPTION OF THE EMBODIMENTS

Figure 1:
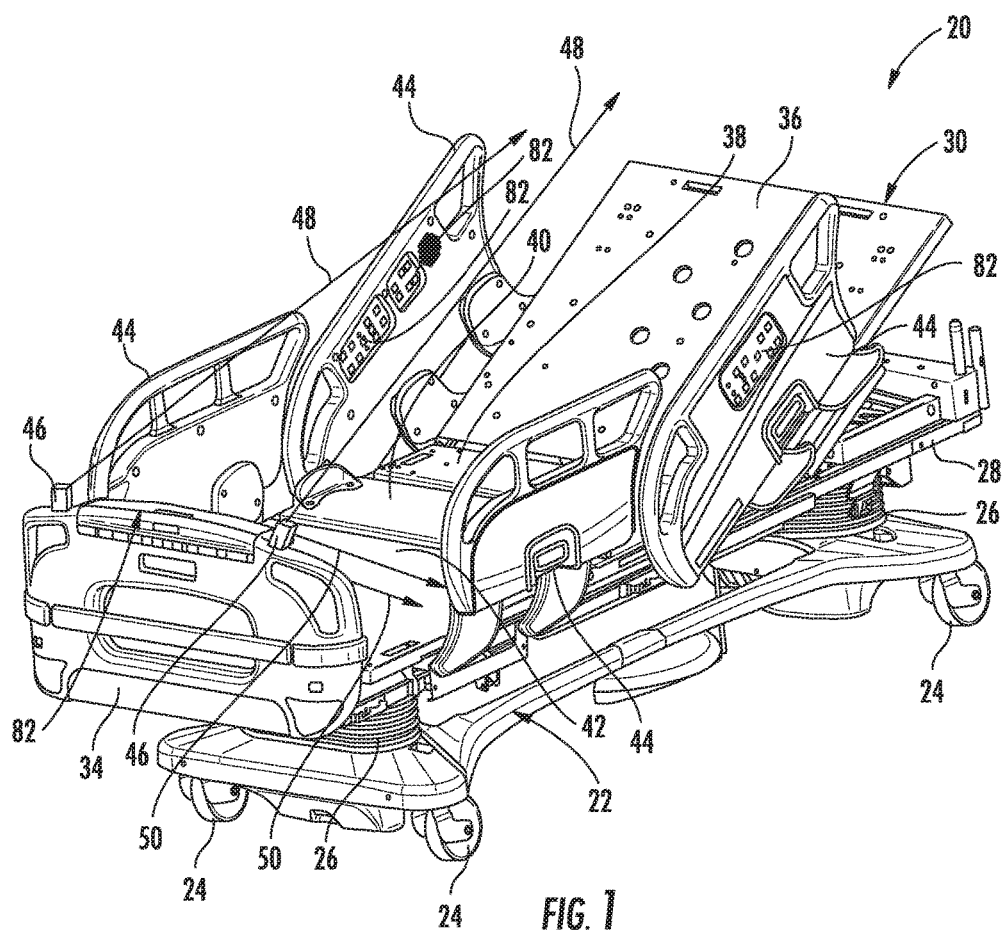
FIG. 1 is a perspective view of one embodiment of a person support apparatus incorporating some aspects of the present disclosure.

A person support apparatus 20 according to one embodiment is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, elevation adjustment mechanisms 26 supported on the base, a frame or litter 28 supported on the elevation adjustment mechanisms, and a support deck 30 supported on the frame. Person support apparatus 20 further includes a headboard 32 and a footboard 34.

Base 22 includes a brake that is adapted to selectively lock and unlock wheels 24 so that, when unlocked, person support apparatus 20 may be wheeled to different locations. Elevation adjustment mechanisms 26 are adapted to raise and lower frame 28 with respect to base 22. Elevation adjustment mechanisms 26 may be hydraulic actuators, electric actuators, or any other suitable device for raising and lowering frame 28 with respect to base 22. In some embodiments, elevation adjustment mechanisms 26 are operable independently so that the orientation of frame 28 with respect to base 22 can also be adjusted.

Frame 28 provides a structure for supporting support deck 30, headboard 32, and footboard 34. Support deck 30 is adapted to provide a surface on which a mattress (not shown), or other soft cushion is positionable so that a person may lie and/or sit thereon. Support deck 30 is made of a plurality of sections, some of which are pivotable about generally horizontal pivot axes. In the embodiment shown in FIG. 1, person support deck 30 includes a head section 36, a seat section 38, a thigh section 40, and a foot section 42. Head section 36, which is also sometimes referred to as a Fowler section, is pivotable between a generally horizontal orientation (not shown in FIG. 1) and a plurality of raised positions (one of which is shown in FIG. 1). Thigh section 40 and foot section 42 may also be pivotable.

A plurality of side rails 44 (FIG. 1) may also be coupled to frame 28. If person support apparatus 20 is a bed, there may be four such side rails, one positioned at a left head end of frame 28, a second positioned at a left foot end of frame 28, a third positioned at a right head end of frame 28, and a fourth positioned at a right foot end of frame 28. If person support apparatus 20 is a stretcher or a cot, there may be fewer side rails. In other embodiments, there may be no side rails on person support apparatus 20. Regardless of the number of side rails, such side rails are movable between a raised position in which they block ingress and egress into and out of person support apparatus 20, and a lowered position in which they are not an obstacle to such ingress and egress.

The construction of any of base 22, elevation adjustment mechanisms 26, frame 28, support deck 30, headboard 32, footboard 34, and/or side rails 44 may take on any known or conventional design, such as, for example, that disclosed in commonly assigned, U.S. Pat. No. 7,690,059 issued to Lemire et al., and entitled HOSPITAL BED, the complete disclosure of which is incorporated herein by reference; or that disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The construction of any of base 22, elevation adjustment mechanisms 26, frame 28, support deck 30, headboard 32, footboard 34 and/or the side rails may also take on forms different from what is disclosed in the aforementioned patent and patent publication.

Person support apparatus 20 of FIG. 1 also includes a pair of thermal sensors 46 that are adapted to detect thermal electromagnetic radiation in the infrared wavelength range. More specifically, although other types of thermal sensors can be used, sensors 46 of FIG. 1 are adapted to detect infrared waves that have wavelengths of between 600 nanometers (nm) to 1 millimeter (mm). In some embodiments, thermal sensors 46 are adapted to detect a smaller range of the infrared spectrum, such as wave having a wavelength of about 3 to 20 micrometers ($\mu$m). These ranges of wavelengths are not intended to be absolute, and any types of sensors that are able to detect and/or generate images or maps from electromagnetic radiation generally outside the visible spectrum are contemplated herein.

Thermal sensors 46 are integrated into footboard 34 and positioned to have a field of view defined generally between an upper line 48 and a lower line 50, as approximately shown in FIG. 1. The precise boundaries of this field of view can vary from that shown. In the embodiment of FIG. 1, the field of view if specifically chosen to be able to detect thermal energy coming from a person positioned on support deck 30, as will be discussed in greater detail below. However, in other embodiments, where thermal sensors 46 may be used to carry out different functions, the fields of view of those sensors 46 can be changed to include regions adjacent the sides of the person support apparatus, regions in front of footboard 34, regions underneath support deck 30 (such as the floor), and still other locations. In the embodiment shown in FIG. 1, the fields of view of each sensor 46 are configured to overlap with each other in the area above the support deck 30 so that the thermal images generated from each sensor 46 of a person on support deck 30 may be correlated with each other in order to generate a stereoscopic thermal image of the person, if present, and/or any other objects that may or may not be within the overlapping field of view.

Although FIG. 1 shows two thermal sensors 46, it will be understood that different numbers of thermal sensors 46 may be used in different embodiments, including embodiments having only a single thermal sensor 46. Further, it will be understood that the position of the thermal sensors 46 on person support apparatus 20 can be varied from that shown in FIG. 1. Thus, for example, instead of mounting thermal sensors 46 on footboard 34, thermal sensors 46 may be incorporated into one or more of the side rails 44, headboard 32 (not shown in FIG. 1, but shown in FIGS. 5-10), or positioned at other locations either on or off of person support apparatus 20.

In one embodiment, each thermal sensor 46 is a thermopile comprising an array of thermal sensing elements that are adapted to generate, in combination, a thermal image 54 (see FIG. 3B) having as many thermal pixels as there are thermal sensing elements 52 in the sensor 46. For example, FIG. 2 shows a thermal sensor 46 comprising a thermopile having a 3 by 3 array of thermal sensing elements 52. Each thermal sensing element 52 is adapted to detect a current temperature within a corresponding location within the field of view of that sensor 46. Thus, in the example shown in FIG. 2, sensor 46 includes nine thermal sensing elements 52, and this sensor 46 will therefore generate a 3×3 thermal image. It will be understood that the set of temperatures shown in FIG. 2 that are detected by the nine thermal sensing elements 52 are an arbitrary set of temperatures that have been selected merely for purposes of illustration. In general, thermal sensors 46 are chosen to be able to sense temperatures over a range that extends both above and below a normal human body temperature (98.6 degrees F. or 37 degree C.) so that the presence or absence of a person can be discerned from temperatures that are associated with non-human objects.

FIG. 3A shows an illustrative visual image 56 of a person 58 positioned on support deck 30 of a person support apparatus, such as, but not limited to, person support apparatus 20. FIG. 3B shows the corresponding thermal image 54 of person 58. That is, thermal image 54 is the thermal image generated by person 58 of FIG. 3A and her surroundings taken from the same location and at the same time as the visual image 56 of FIG. 3A was generated. As can be seen, both visual image 56 and thermal image 54 are 8 by 8 images. Further, as can be seen, those thermal sensing elements 52 corresponding to the person's head and right hand have detected the highest temperatures of thermal image 54; those thermal sensing elements 52 generally corresponding to the regions of the person's body that are covered with a blanket have detected the second highest temperatures of thermal image 54; those thermal sensing elements 52 generally corresponding to the regions around the immediate periphery of the person's body have detected the third highest temperatures of thermal image 54; and those thermal sensing elements 52 generally corresponding to the remaining regions have detected the coolest temperatures of thermal image 54.

Figure 4:
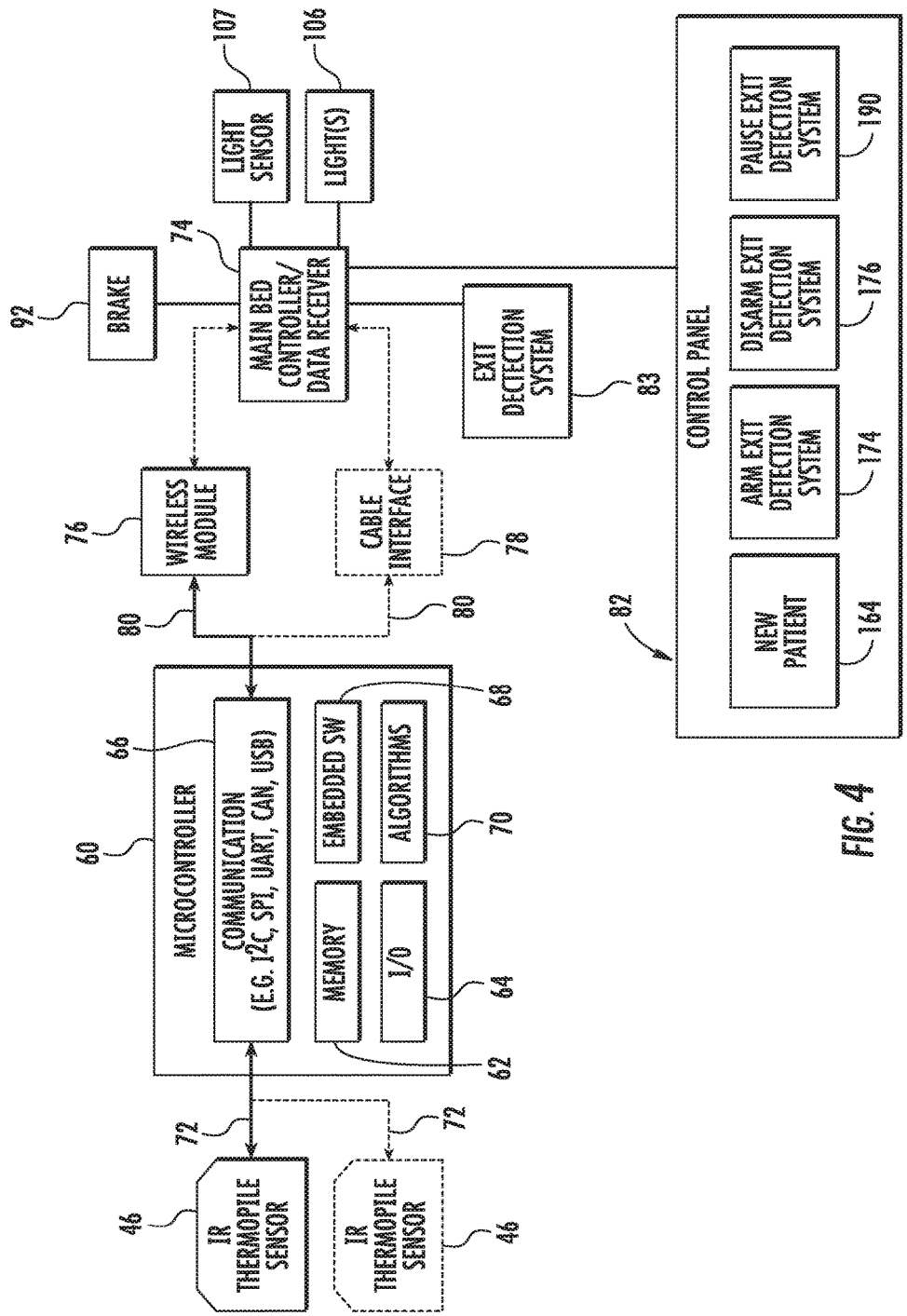
FIG. 4 is a diagram of an illustrative set of components that may be partially or wholly incorporated into any of the person support apparatuses described herein.

The thermal images 54 detected by thermal sensor 46 are processed by a controller 60 in order to carry out one or more of the functions described herein. FIG. 4 illustrates one example of a controller 60 that is suitable for carrying out such analysis. In the embodiment shown, controller 60 is a conventional microcontroller having a memory 62, one or more inputs/outputs 64, a communication module 66, and embedded software 68 suitable for carrying out one or more algorithms 70, as will be discussed in greater detail below. Other variations of controller 60 are, of course possible. For example, controller 60 may be implemented as a combination of multiple microcontrollers, or it may be implemented as one or more microprocessors, and/or it may be implemented using other programmable electronics that are programmed to carry out the functions described herein.

In still other variations, controller 60 may be implemented to include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on person support apparatus 20, or they may reside in a common location on person support apparatus 20, or in still other embodiments they may partially or completely be located somewhere off of person support apparatus 20. When physically distributed, the components may communicate using any suitable serial or parallel communication protocol, such as, but not limited to, CAN, LIN, Firewire, I-squared-C, RS-232, RS-485, etc.

As shown in FIG. 4, controller 60 is in communication with one or more thermal sensors 46 via one or more communication lines 72. Communication lines 72 may be cables, wires, optical fibers, wireless channels, or other types of communication lines. Thermal sensors 46 repetitively forward the data comprising the thermal images 54 to controller 60 for storage and processing. Controller 60 receives this information from communication line 72 via communication module 66. Controller 60 also uses communication module 66 to communicate with a main controller 74 on person support apparatus 20. Such communication can take place using a wireless module 76 that enables wireless signals to pass between main controller 74 and controller 60, or it may take place via a cable interface 78 that enables wired signals to pass between main controller 74 and controller 60. Controller 60 communicates with either wireless module 76 or cable interface 78 via a wired communication line 80 that is implemented as a wire, cable, optical fiber, or other type of connection.

Main controller 74 is responsible for carrying out and/or overseeing the functions associated with person support apparatus 20 that are separate from the thermal image processing carried out by controller 60. For example, when person support apparatus 20 is implemented as a bed, such as shown in FIG. 1, main controller 74 is responsible for overseeing and/or controlling one or more of the following functions: pivoting head section 36; pivoting thigh and/or foot sections 40 and 42, respectively; raising and lowering support deck 30 via elevation adjustment mechanisms 26; controlling one or more lights 106, indicators, and/or alarms on person support apparatus; communicating with a light sensor 107; communicating with a plurality of control panels 82 on person support apparatus 20 (FIG. 1) and appropriately responding to user commands received from the control panels 82; and communicating with an exit detection system 83 and/or scale system, if person support apparatus 20 is equipped with one or both of these. Main controller 74 may also be configured to carry out other functions. Further, in at least one embodiment, main controller 74 may also be configured to carry out the image processing functions of controller 60 so that controller 60 is eliminated and its function is subsumed by main controller 74. Still other variations are possible.

It will be understood by those skilled in the art that the components illustrated in FIG. 4 are not all necessarily needed, used, and/or present on a patient support apparatus when carrying out the algorithms discussed herein. Instead, certain ones of the algorithms disclosed herein may be implemented on a patient support apparatus that only includes a subset of the components shown in FIG. 4. Other algorithms may be implemented on a patient support apparatus that only includes a different subset of the components of FIG. 4. Thus, as but one example, lights, such as lights 106, are necessarily included on at least one embodiment of person support apparatus 20b (FIG. 6) when carrying out automatic lighting control algorithm 70b (FIG. 12), while the light sensor 107 and various other components (e.g. exit detection system 83, brake 92, etc.) may or may not be present on person support apparatus 20b. The various patient support apparatuses (e.g. 20a-f) described herein therefore need not include all of the components of FIG. 4.

Controller 60 (FIG. 4) is configured to carry out one or more functions based upon the analysis of thermal images from one or more sensors 46. In some cases, the function is carried out solely based upon the analysis of the thermal images and without regard to any other sensor information. However, in other cases, one or more functions may be carried out in conjunction with one or more additional types of sensor wherein the additional sensor data is correlated, fused, or otherwise used in conjunction with the thermal image data. FIGS. 5-10 illustrate six different person support apparatuses 20a-f that are each configured to carry out individual algorithms 70a-f, respectively. Algorithms 70a-f are illustrated in more detail in FIGS. 11-16, respectively. An alternative embodiment of algorithm 70f is shown in FIG. 17 and may be carried out on person support apparatus 20f. Although FIGS. 5-10 each illustrate a single person support apparatus configured to carry out a single one of algorithms 70a-g, it will be understood that any one or more of the various algorithms 70a-g described herein can be combined with any others of these algorithms on the same person support apparatus. Thus, for example, person support apparatus 20a of FIG. 5 could be modified to also perform, in addition to algorithm 70a, the algorithm 70b (FIG. 12) that is carried out by person support apparatus 20b (FIG. 6). Similarly, person support apparatus 20 of FIG. 1 may include any one or more of algorithms 70a-70g. Still further, any of the person support apparatuses described herein may be configured to include still other algorithms that have not been provided with a specific reference number, either alone or in combination with algorithms 70a-70g.

Figure 5:
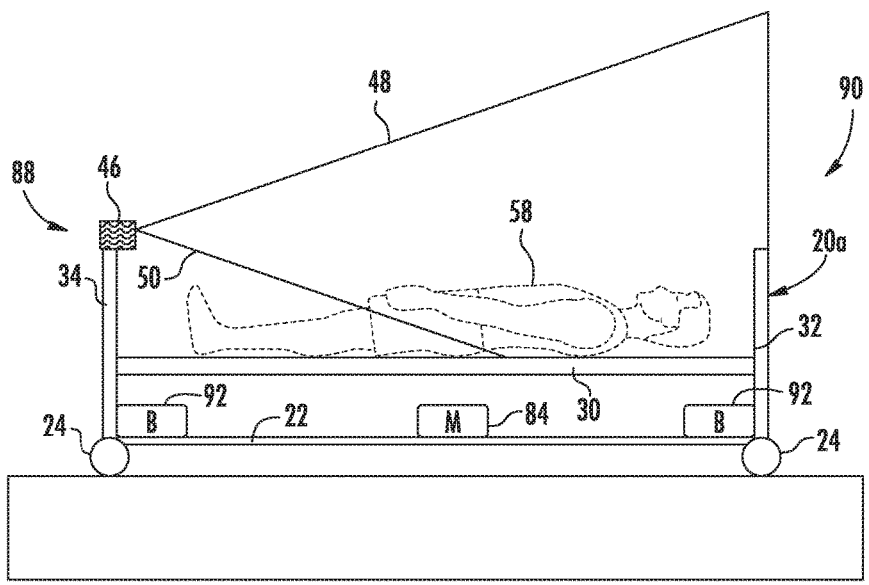
FIG. 5 is side, elevation diagram of an embodiment of a person support apparatus incorporating a brake-enable feature.
Figure 6:
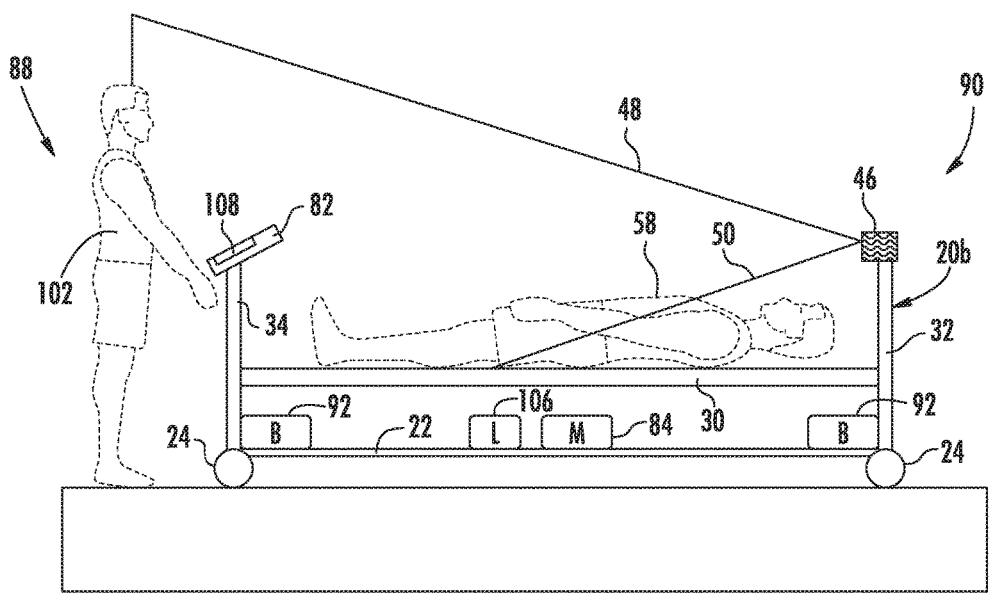
FIG. 6 is a side, elevation diagram of an embodiment of a person support apparatus incorporating an automatic display and/or lighting control feature.

Person support apparatus 20a of FIG. 5, like person support apparatus 20, is a bed that includes a base 22, wheels 24, a support deck 30, a headboard 32, and a footboard 34. Person support apparatus 20a also includes a plurality of brakes 92 that selectively brake and unbrake wheels 24 when activated and deactivated by a user. Such activation and deactivation is carried out electrically in person support apparatus 20a. That is, person support apparatus 20a includes a button or switch (not shown) that a user may press or manipulate in order to activate and deactivate the brakes 92. Person support apparatus 20a further includes a motor 84 that is adapted to power one or more of the wheels 24 of person support apparatus 20a such that a user does not need supply all of the force necessary to move person support apparatus 20a from one location to another. Motor 84 is therefore part of a propulsion system that reduces the effort needed by a user to wheel person support apparatus 20a from one location to another. Examples of such a propulsion system are disclosed in commonly-assigned co-pending U.S. patent application Ser. No. 13/795,193 filed Mar. 12, 2013 and entitled POWERED PATIENT SUPPORT APPARATUS (inventors Richard Derenne et al.), the complete disclosure of which is hereby incorporated herein by reference. Other types of propulsion systems may be used. Further, in person support apparatuses 20a, 20b, 20c, and 20e, motor 84 and its corresponding propulsion system are optional components that do not interact with controller 60, and therefore can be omitted, if desired.

Although not show in FIG. 5, person support apparatus 20a includes controller 60. Further, controller 60—when incorporated into person support apparatus 20a—includes the instructions necessary for carrying out algorithm 70a stored in its memory 62. Algorithm 70a is an automatic braking algorithm that is designed to avoid having the brakes 92 deactivated while a person is supported on support deck 30 of person support apparatus 20a and person support apparatus 20a is not being moved between locations. In other words, algorithm 70a is designed to automatically apply the brakes 92 after person support apparatus 20a has been moved to a desired location in case the caregiver, or other person who pushed person support apparatus 20a to the desired location, forgets to. Applying the brakes 92 helps prevent individuals who use person support apparatus 20a from falling when either entering or exiting the support deck 30 by ensuring that person support apparatus 20a remains stable and does not move during such times of entry and exit.

Figure 11:
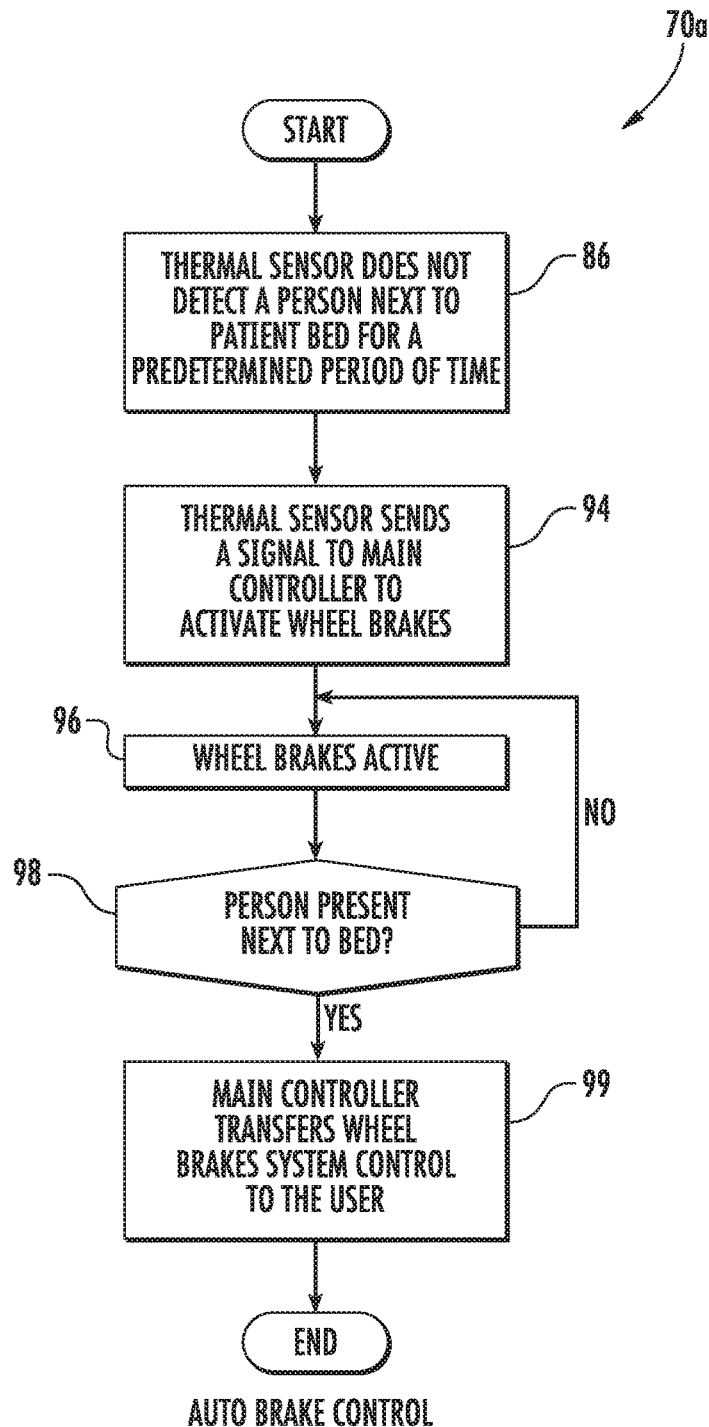
FIG. 11 is a flowchart of an illustrative algorithm carried out by the person support apparatus of FIG. 5.

As shown in FIG. 11, automatic braking algorithm 70a begins at an initial step 86 where controller 60 determines whether a threshold amount of time has passed since any person was detected within the vicinity of—but excluding support deck 30—person support apparatus 20a. In other words, controller 60 determines whether any person other than a person positioned on support deck 30 has been detected in the vicinity of person support apparatus 20a within the last X number of minutes where "X" refers to the threshold amount of time. Controller 60 determines whether a person has been detected by analyzing the thermal images captured by thermal sensor 46, which is positioned on person support apparatus 20a. Thermal sensor 46 repetitively captures (such as several times per minute, or at any other suitable rate) thermal images 54 of the vicinity of person support apparatus 20a and forwards those images to controller 60 for processing.

Although FIG. 5 illustrates a field of view for sensor 46 having top and bottom boundary lines 48 and 50 that are focused on the area of support deck 30, it will be understood that these boundary lines are merely for illustrative purposes and that the field of view of sensor 46 will include not only the area of support deck 30, but also a foot end area 88 positioned adjacent footboard 34, a head end area 90 positioned adjacent headboard 32, and areas along both sides of person support apparatus 20a. In other words, sensor 46 includes one or more fields of view that capture those areas adjacent person support apparatus 20a where a caregiver, assistant, or other person attending to the occupant of person support apparatus 20a would likely be standing while interacting with the occupant of person support apparatus 20a. In some embodiments, multiple sensors 46 may be positioned on person support apparatus 20a in order to monitor and capture thermal images from all of these adjacent areas.

Controller 60 determines whether a person is positioned in any of these areas (foot end area 88, head end area 90, and both side areas) by analyzing the thermal images 54 supplied from thermal sensor 46. That is, controller 60 examines thermal images 54 to determine if temperatures are detected within the thermal image that have values that are likely the result a person being positioned within the thermal sensor 46's field of view. In some embodiments, controller 60 is further programmed to determine the collective shape of the thermal pixels that are detecting temperature readings that are likely to be the result of a person. Controller 60 then compares these shapes and their relative position within the field of view to better assess whether the images correspond to a person, or some other source of heat. Still further, controller 60 may be programmed to take into account any movement of the pixels having temperatures corresponding to human temperatures, and to use that movement data to better distinguish between stationary heat sources, such as inanimate electrical devices (e.g. medical or therapy device, or other devices that emit heat) and human beings. In other words, stationary sources of heat are more likely to be the result of an inanimate heat-emitting object than a person. Alternatively, moving sources of heat are more likely to be the result of a person rather than a heat-emitting device.

Further, controller 60 may take into account any changes in the intensity of the thermal pixels in order to be able to better distinguish between inanimate objects and persons. That is, heat emitting devices such as electrical appliances, medical devices, etc. will tend to start out at relatively cooler temperatures when first activated and to gradually increase their heat output as they continue to operate for longer periods of time. The heat signature of individuals, however, will tend to stay more constant. Controller 60 therefore not only analyzes the currently detected heat intensities to determine whether a person is detected within the relevant fields of view, but also compares the heat intensities to prior thermal images taken within the same fields of view. To the extent the heat intensities are determined to be changing over time by an amount greater than what would normally be expected from a person, this factor is used by controller 60 to distinguish between persons and objects within sensor 46's field of view. Still other techniques and steps for distinguishing between humans and inanimate objects, as well as identifying and tracking the movement of an individual based on his or her heat signature, are known to those skilled in the art and can be used by controller 60.

After determining at step 86 whether or not a person has been detected within the vicinity of person support apparatus 20a, controller 60 moves onto step 94 (FIG. 11). At step 94, controller 60 sends a message to main controller 74 instructing it to activate the brakes 92 (to the extent they are not already activated). Controller 60 responds by activating brakes 92 so that wheels 24 of person support apparatus 20a are not able to freely roll, thereby ensuring that the person support apparatus 20a remains stationary and stable during any attempted exit or entry by an occupant of person support apparatus 20a. This activation of brakes 92 is performed at step 96 by main controller 74.

After step 96, controller 60 continues to monitor the vicinity of person support apparatus 20a to determine whether a person is detected in that vicinity or not. This continued monitoring takes place at step 98. If no person is detected, the brakes remain active, as represented by step 96. If a person is detected, however, controller 60 sends a signal to main controller 74 at a step 99 indicating that a person has been detected within the vicinity of person support apparatus 20a. Main controller 74 responds to this message by allowing the status of brakes 92 to be changed by the person whose presence has been detected within the vicinity of person support apparatus 20a. Step 99 therefore does not result in the deactivation of the brakes 92, but instead results in allowing the brakes to be deactivated by the person if that person desires to do so. If such deactivation is desired, the person simply presses on the appropriate button, switch, lever, or other input on one of control panels 82 that controls the brakes 92. Alternatively, if person support apparatus 20a includes a non-electric brake actuator, such as a pedal or the like, the person can manually release the brakes by activating the non-electric brake actuator.

In some embodiments, the completion of step 99 is automatically followed by starting algorithm 70a over again at step 86. That is, once the control of the brakes has been transferred back to the user at step 86, controller 60 begins monitoring the output of thermal sensor 46 at step 86 and checking to see if the person within the vicinity of person support apparatus 20 has departed for longer than the threshold amount of time. When that event is detected, control passes to step 94 and continues in the manner previously described.

It will be understood that the precise value of the threshold amount of time used by controller 60 at step 86 can be varied. In one embodiment, the threshold is set to a fraction of a minute, such as half a minute. In other embodiments, the threshold is set to a few minutes. Other values can, of course, be used.

Algorithm 70a can, of course, be modified from the specific steps shown in FIG. 11 in a number of manners. In one modified version of algorithm 70a, the algorithm only includes steps 86, 94, and 96. In this modified version, controller 60 only determines whether a person has left the vicinity of person support apparatus 20a for the threshold amount of time (step 86), notifies main controller 74 of that fact (step 94), and main controller 74 then activates the brakes 92 if they are not already activated (step 96). Thereafter, the modified algorithm 70a terminates and does not begin again until the brake has been disengaged. Such disengagement is sensed by a brake sensor (not shown) that is either in communication with controller 60 or main controller 74 (or both). Upon the disengagement of the brake, controller 60 re-commences operation of the modified algorithm 70a at step 86. Modified algorithm 70a therefore ensures that the brakes will always be subsequently activated after deactivation whenever a person has left the vicinity of person support apparatus 20a for the threshold amount of time.

Figure 12:
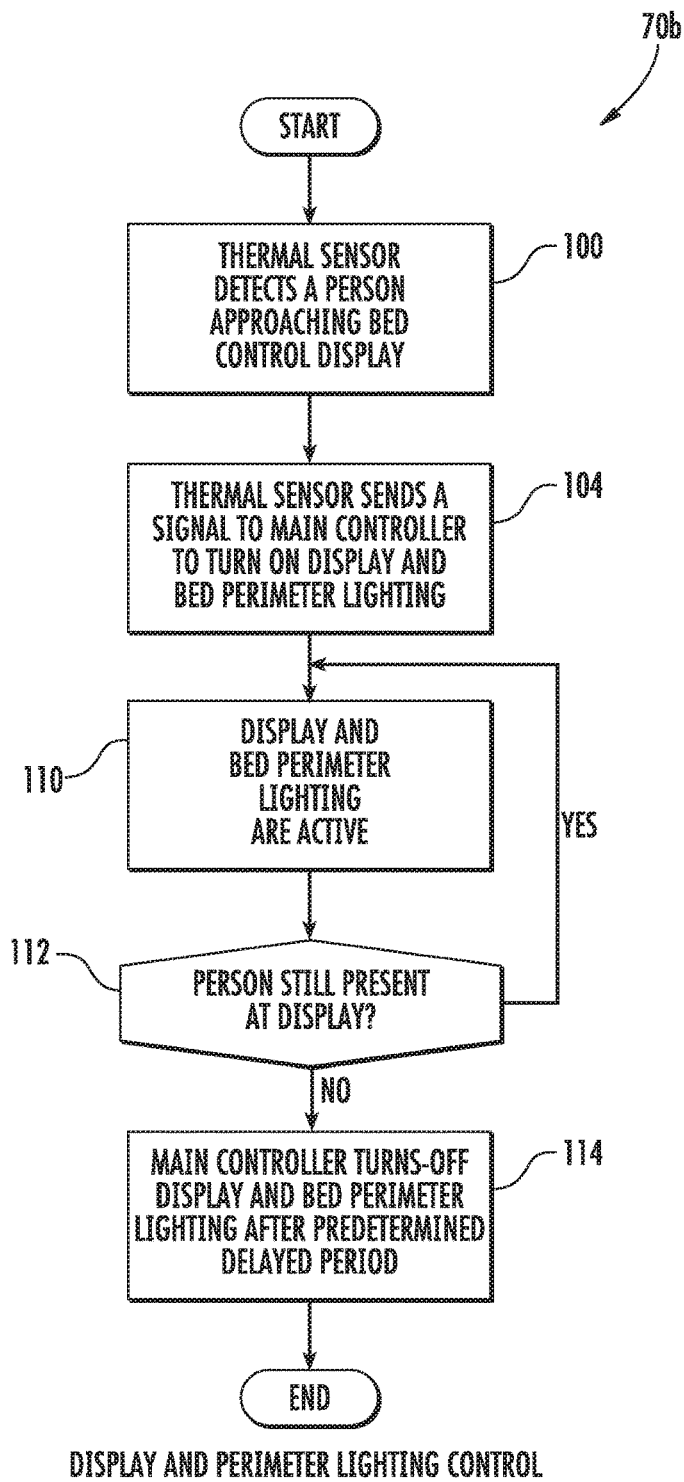
FIG. 12 is a flowchart of an illustrative algorithm carried out by the person support apparatus of FIG. 6.

FIG. 6 illustrates another person support apparatus 20b that is configured to carry out an automatic lighting control algorithm 70b. One embodiment of the automatic lighting control algorithm 70b is shown in FIG. 12. Automatic lighting control algorithm 70b is generally designed to automatically turn on appropriate lighting (e.g. lights 106 of FIG. 4) on or adjacent to person support apparatus 20b when a person, such as a caregiver in a healthcare setting, approaches the vicinity of person support apparatus 20b. In addition to being a convenience to the caregiver to have appropriate lighting automatically provided, such automatic lighting can allow, in some cases, the caregiver to carry out his or her assigned task without having to touch one or more controls on the person support apparatus 20b, thereby reducing the risk of an infection spreading. In some cases, the automatic lighting includes lighting around the perimeter of person support apparatus 20b, while in other cases the lighting includes the automatic illumination of an LCD screen, touch screen, or other display on person support apparatus 20b, while in still other cases the automatic lighting includes both of these and/or other forms of automatic lighting.

With reference to FIGS. 6 and 12, automatic lighting algorithm 70b begins at an initial step 100 where controller 60 detects the presence of a person approaching person support apparatus 20b. This is accomplished through the use of one or more thermal sensors 46 (FIG. 6) positioned on support apparatus 20b. FIG. 6 illustrates a single thermal sensor 46 coupled to headboard 32 of person support apparatus 20b that has a field of view generally configured to detect the presence of a caregiver 102 positioned in foot end area 88 of person support apparatus 20b. It will be understood that the position of thermal sensor 46 on person support apparatus 20b can be changed. Further, it will be understood that additional thermal sensors 46 can be added to person support apparatus 20b to increase and/or change the collective field of view sensed by the multiple thermal sensors 46. In the embodiment shown in FIG. 6, the mounting of thermal sensor 46 on headboard 32 allows thermal sensor 46 to capture thermal images not only of occupant 58 of person support apparatus 20b, but also a caregiver 102 positioned within the foot end area 88 or along the sides of person support apparatus 20b.

Controller 60 carries out step 100 in a similar manner to how it carries out step 86 in algorithm 70a. That is, controller 60 analyzes the thermal images from thermal sensor 46 to determine whether or not a heat pattern corresponding to the presence of a person outside of support deck 30 is present within the thermal images. Once such a heat pattern is detected, controller 60 moves to step 104 where it sends a message to main controller 74 instructing it to illuminate one or more perimeter lights 106 and a display 108 mounted to a footboard control panel 82 in the example illustrated in FIG. 6.

Perimeter lights 106 are mounted at one or more locations on person support apparatus 20b where they provide illumination of the floor areas around the perimeter of person support apparatus 20b. In this manner, they help an approaching caregiver see any obstructions that might be present on the floor. Further, perimeter lights 106 are generally configured so that, when illuminated, their light does not provide any substantial illumination of the area on top of support deck 30 where an occupant 58 may be present. In this manner, perimeter lights 106 are unlikely to cause any visual disturbances to a sleeping or resting occupant of person support apparatus 20b.

Display 108 may take on different forms, such as one or more Liquid Crystal Displays (LCDs); one or more touch screens; a set of backlit buttons, switches, or other inputs; or still other forms. Oftentimes display 108 will be mounted to footboard 34. However, it will be understood that display 108 may be positioned elsewhere on person support apparatus 20b, and that, in some embodiments, there may be multiple displays 108 positioned in different locations that are controlled during execution of algorithm 70b.

At step 110, main controller 74 illuminates the perimeter lights 106 and the display 108. When display 108 includes one or more LCDs or touch screens capable of displaying different information thereon, main controller 74 is programmed, in at least one embodiment, to not only illuminate the display, but to also select what information is to be displayed thereon. The choice of which information is displayed at step 110 is configurable by a user in one embodiment. In such an embodiment, a user is able to select the displayed information prior to execution of algorithm 70b so that the selected information will automatically be displayed upon any subsequent executions of algorithm 70b without requiring any input from the user. In another embodiment, main controller 74 is pre-programmed to select certain status information regarding person support apparatus 20b that will be automatically displayed at step 110. Such pre-programmed status information includes information that a caregiver would likely be interested in knowing, such as, but not limited to, any one or more of the following: the status of brakes 92; the status of exit detection system 83 (i.e. whether armed or not) if such a system is included on person support apparatus 20b; the status of any control lockouts on person support apparatus 20b that prevent an occupant of support apparatus 20b from changing aspects of the person support apparatus 20b (e.g. the height of support deck 30 and/or the angle of any of deck sections 36, 38, 40, and/or 42); a weight of the occupant (if a scale system is included on person support apparatus 20b); an angle of head section 36; and any information that may be stored on person support apparatus 20b concerning medical care protocols that have been taken with regard to occupant 58 or that are desired to be taken (e.g. whether occupant 58 has been turned or bathed); and/or other information.

After the illumination is provided at step 110 (FIG. 12), controller 60 proceeds to step 112 where it continues to analyze the incoming thermal images from thermal sensor 46 to determine whether the caregiver 102 is still within the vicinity of person support apparatus 20b. If caregiver 102 is still present, control returns to step 110 and the illuminated lighting continues to be illuminated. If caregiver 102 is no longer detected, control passes to step 114 where controller 60 continues to check for the presence and/or absence of caregiver 102 for a predetermined amount of time. If the caregiver remains absent for the predetermined amount of time, then controller 60 sends a message to main controller 74 instructing it to turn off the illumination of perimeter lights 106 and display 108. The predetermined period of time can vary, but is generally selected so that the lights 106 and display 108 do not immediately shut off if the caregiver 102 briefly steps out of the field of view of thermal sensor 46 but returns sooner than the predetermined time period.

As with algorithm 70a, algorithm 70b can be modified in various manners. In one modified version, person support apparatus 20b includes at least one ambient light sensor 107 (FIG. 4) adapted to detect the amount of ambient light around person support apparatus 20b. The output of ambient light sensor 107 is fed to controller 60 and/or main controller 74. If ambient light sensor 107 detects an amount of light consistent with it being daytime, or consistent with the room already being lit by external lights (e.g. overhead lights), then controller 60 does not send any message to main controller 74 to turn on either perimeter lights 106 or display 108. Indeed, in this modified version, ambient light sensor 107 may be the trigger for controller 60 to begin executing algorithm 70b. In other words, controller 60 can be configured to only execute algorithm 70b when it receives a signal from the ambient light sensor indicating a relatively low level of ambient light in the vicinity of person support apparatus 20b.

In still another modified version of algorithm 70b, controller 60 separates the automatic illumination of display 108 from the automatic illumination of perimeter lights 106 based on the output of ambient light sensor 107. In this other modified version, controller 60 executes algorithm 70b in the manner shown in FIG. 12 for display 108 regardless of the output of ambient light sensor 107, and only executes algorithm 70b in the manner shown in FIG. 12 for perimeter lights 106 if ambient light sensor 107 indicates a relatively low level of light. As a result, display 108 will always be illuminated automatically when a caregiver 102 enters the field of view of thermal sensor 46 regardless of ambient light conditions, but perimeter lights 106 will only be illuminated automatically if the caregiver enters the field of view of thermal sensor 46 during low, or dark, levels of ambient lighting. This modified version ensures that a caregiver will always automatically be presented with the information on display 108 when he or she approaches, but will only be presented with automatic perimeter lighting if the room is otherwise dark. Still other variations are, of course, possible.

Figure 7:
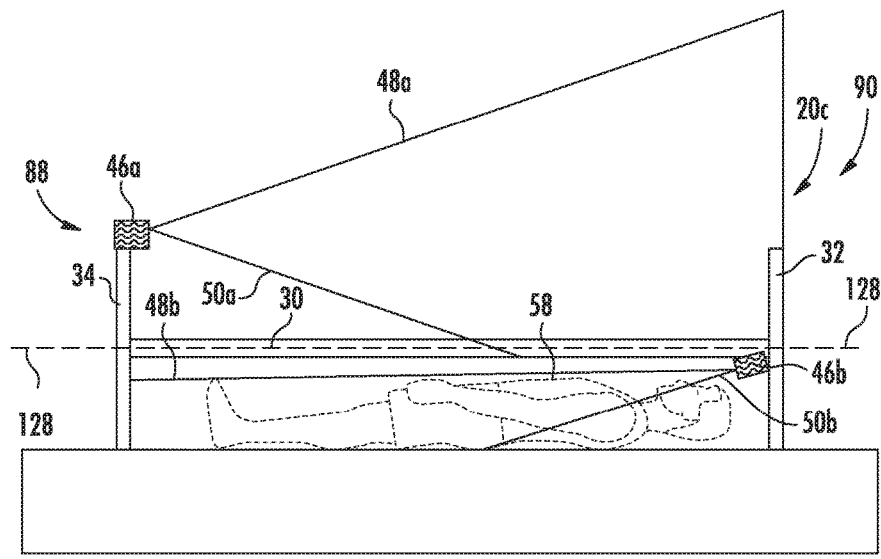
FIG. 7 is a side, elevation diagram of an embodiment of a person support apparatus incorporating a fallen person detection feature.
Figure 13:
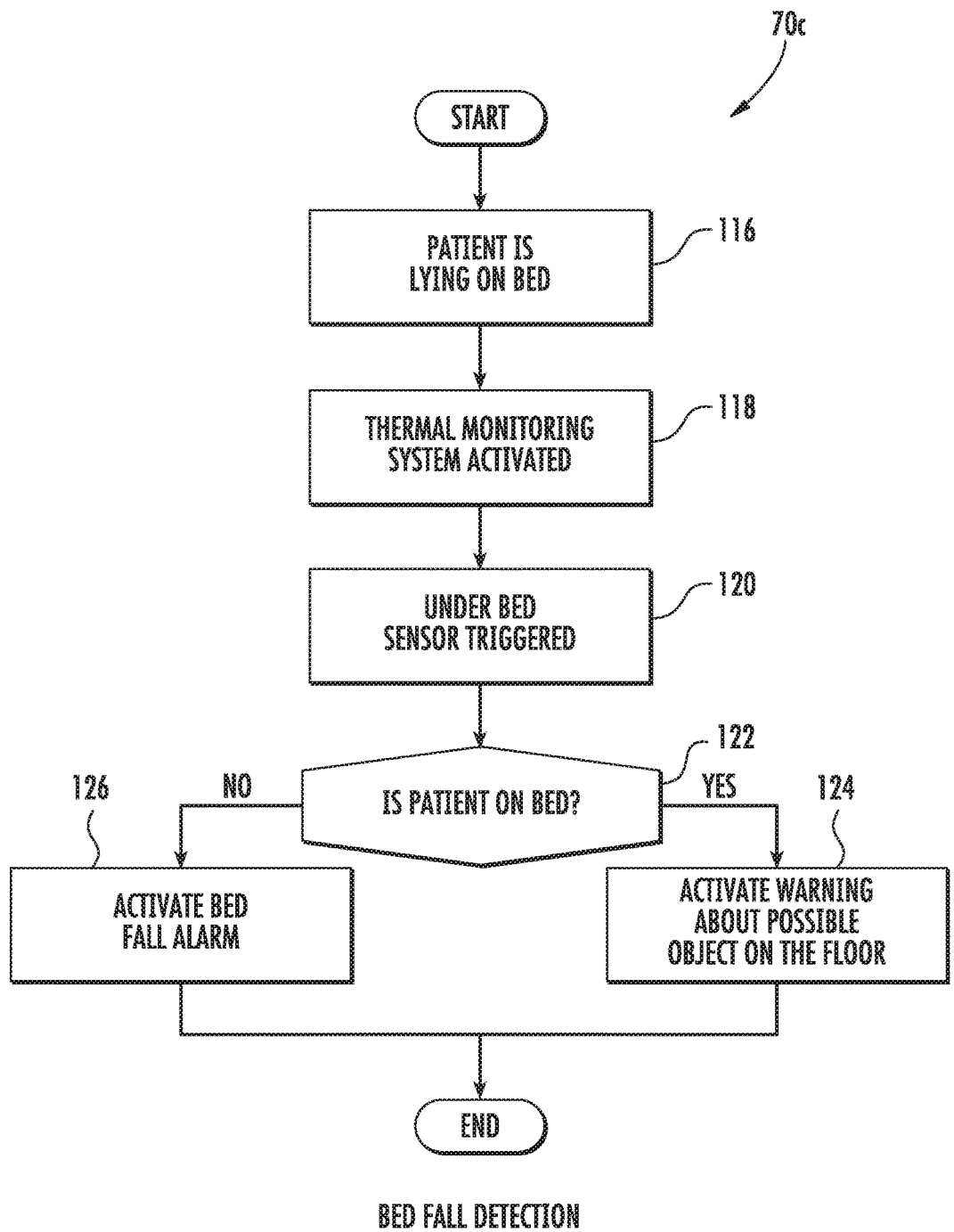
FIG. 13 is a flowchart of an illustrative algorithm carried out by the person support apparatus of FIG. 7.

FIG. 7 illustrates another person support apparatus 20c that is configured to carry out an automatic fall detection algorithm 70c. One embodiment of the automatic fall detection algorithm 70c is shown in FIG. 13. Automatic fall detection algorithm 70c is generally designed to detect when a person has actually fallen within the vicinity of person support apparatus 20c and to provide notification to one or more persons of that detected fall so that proper assistance can be provided to the fallen individual on a timely basis. Automatic fall detection algorithm 70c is therefore useful in mitigating any injuries that an individual might sustain from the fall.

With reference to FIGS. 7 and 13, automatic fall detection algorithm 70c begins at an initial step 116 when a person 58 is positioned on support deck 30 of support apparatus 20c. In the embodiment of FIGS. 7 and 13, the occupancy of person support apparatus 20c is detected by one or more weight sensors (not shown) that are incorporated into person support apparatus 20c. Such weight sensors may be configured as a plurality of load cells that detect the gravitational force exerted on an occupant of support deck 30. One example of such a load cell based weight detection system is disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. Other types of occupancy detection systems can be used for carrying out step 116 of algorithm 70c.

After the completion of step 116, controller 60 moves onto step 118 where it activates the thermal sensors 46 that are supported on person support apparatus 20c (FIG. 7). In the embodiment shown in FIG. 7, person support apparatus 20c includes two thermal sensors 46a and 46b. Thermal sensor 46a is positioned on footboard 34 and has a field of view defined by boundary lines 48a and 50a that is designed to capture thermal images of an occupant 58 of person support apparatus 20c while the occupant 58 is supported on supported deck 30. Thermal sensor 46b is positioned underneath support deck 30 and has a field of view defined by boundary lines 48b and 50b that is designed to capture thermal images of a person who is positioned on the floor on either side of person support apparatus 20c. Although the field of view of lower thermal sensor 46b is illustrated in FIG. 7 as not capturing foot end area 88 and head end area 90, it will be understood that this field of view can be modified to capture either or both of these areas, if desired, or additional thermal sensors 46 can be added to capture either or both of these areas, if desired.

After thermal sensors 46a and 46b are activated at step 118, controller 60 moves to step 120 where it monitors the thermal images generated by lower thermal sensor 46b and determines whether any thermal images are captured that are suggestive of a human presence within the field of view of thermal sensor 46b. Controller 60 continues with this monitoring until a thermal image is captured that contains heat data suggestive of a human presence. When such a thermal image is captured, controller 60 moves to step 122 where it re-checks the occupancy status of support deck 30. That is, controller 60 checks the outputs from the load cell system to see if a person's weight is still being detected on support deck 30, if such a load cell system is present, or controller 60 analyzes the thermal images from upper thermal sensor 46a to determine if those images correspond to the presence or absence of an occupant on support deck 30. Either method, or still other methods, may be utilized by controller 60 to determine the occupancy status at step 122.

If controller 60 determines at step 122 that an occupant is still positioned on support deck 30, it moves to step 124. At step 124, controller 60 issues a warning that a potential obstacle has been detected by lower thermal sensor 46b. This warning may be an audio warning, a visual warning, or a combination of the two. In one embodiment, the warning includes a message being sent from person support apparatus 20c to a remote location, such as to one or more computers at a nurse's station within a healthcare facility. Such notification can prompt a nurse or other caregiver to investigate the possible obstacle and remove it, as appropriate, so that the likelihood of a person tripping and/or falling over the obstacle is removed.

If controller 60 determines at step 122 that an occupant is no longer present on support deck 30, controller 60 moves to step 126 where it activates a fall alarm. As with the obstacle alarm of step 124, the fall alarm activated at step 126 may be audio, visual, or a combination of the two. Further, it may include sending a message to a remote location, such as a nurses' station within a medical facility. Controller 60 issues the alarm at step 126 on the assumption that, because an occupant is no longer on support deck 30, but a heat pattern suggestive of a person is now being detected on the floor (via lower sensor 46b), it is likely that the heat pattern has resulted from the occupant leaving support deck 30 and having fallen to the floor. After steps 124 or 126, algorithm 70c terminates until it is restarted at step 116.

Various modifications can, of course, be made to algorithm 70c for automatically detecting a person's fall. In one variation, controller 60 analyzes thermal images from one or more thermal sensors (such as sensors 46a and 46b and/or other sensors) to determine whether any heat patterns are detected above a threshold height 128 (FIG. 7) that are suggestive of a person. If any such heat pattern is detected, the movement of that heat pattern is monitored and tracked to determine if its height ever falls below threshold height 128 for at least a minimum amount of time. If such a movement below the threshold 128 is detected for greater than the minimum amount of time, controller 60 concludes that the change in height of the heat pattern is the result of an individual having fallen. Controller 60 then activates the bed alarm in accordance with step 126. In carrying out this modified algorithm, the minimum amount of time is a predetermined value that helps reduce false fall alarms that might be generated due to a person temporarily bending down below that threshold height 128 and then standing up again. Other variations of fall detection algorithm 70c can, of course, be used.

Figure 8:
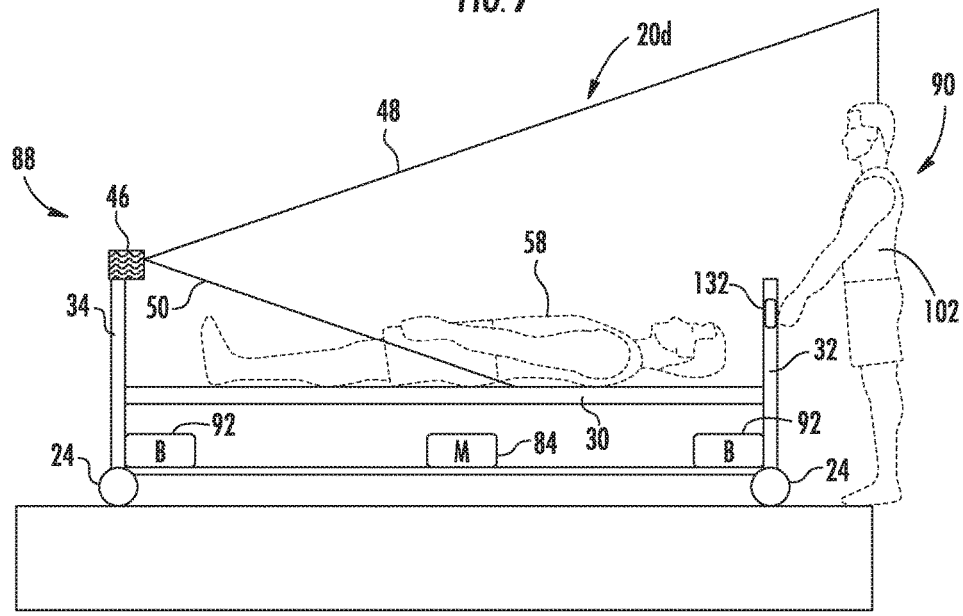
FIG. 8 is a side, elevation diagram of an embodiment of a person support apparatus incorporating a propulsion control feature.
Figure 14:
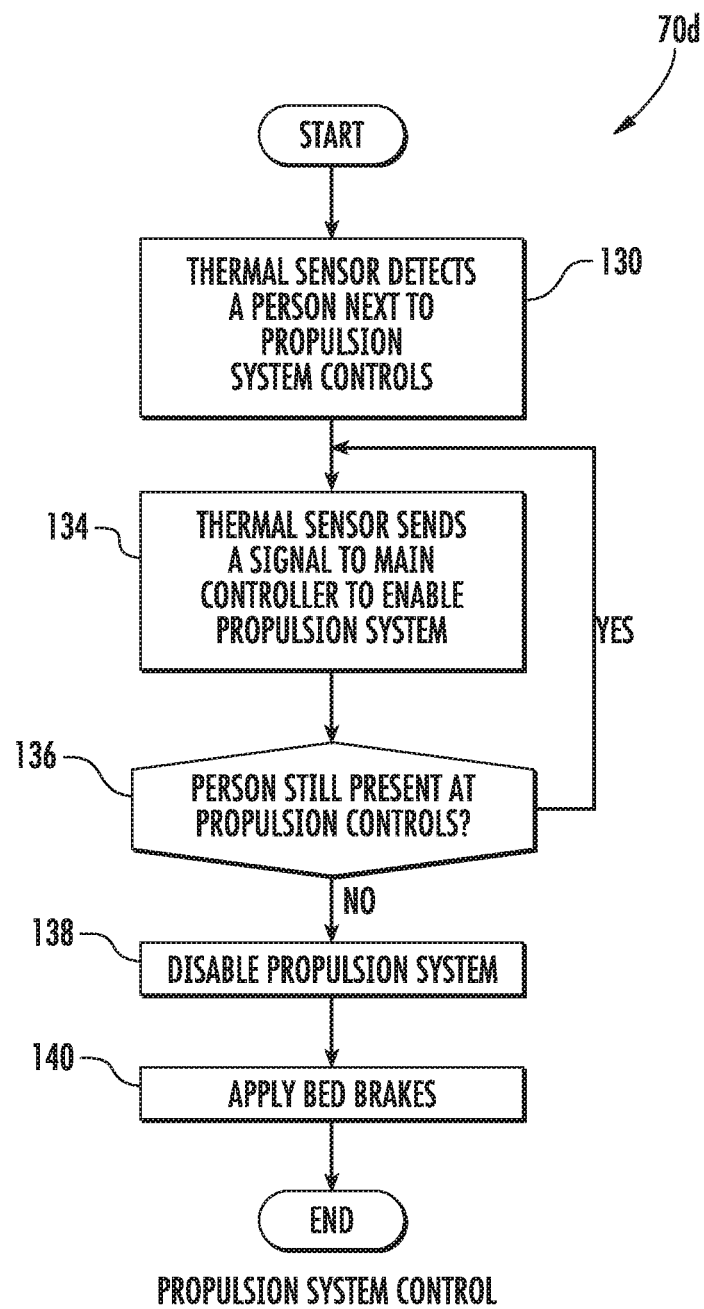
FIG. 14 is a flowchart of an illustrative algorithm carried out by the person support apparatus of FIG. 8.

FIG. 8 illustrates another person support apparatus 20d that is configured to carry out a propulsion enable algorithm 70d. One embodiment of the propulsion enable algorithm 70d is shown in FIG. 14. Propulsion enable algorithm 70d is generally designed to selectively enable and disable an automatic propulsion system based upon the continued presence of an individual within the vicinity of the propulsion system controls. Propulsion enable algorithm 70d therefore operates as a safety mechanism to help prevent unsafe or accidental operation of the propulsion system.

With reference to FIGS. 8 and 14, propulsion enable algorithm 70d begins at an initial step 130 where thermal sensor 46 (FIG. 8) detects the presence of a person within the vicinity of a control input 132 to the propulsion system. In the example shown in FIG. 8, control input 132 is coupled to headboard 32 and thermal sensor 46 includes a field of view large enough to encompass the head end area 90, which is where a person stands in order to access control input 132. Control input 132 may comprise one or more bars, levers, buttons, switches, or the like for controlling motor 84. Motor 84, as previously noted, selectively powers one or more of the wheels 24 on person support apparatus 20d, thereby reducing the effort needed by a person to move support apparatus 20d from one location to another. Because thermal sensor 46 is positioned on footboard 34, its field of view is large enough to also encompass support deck 30 in addition to head end area 90. Controller 60 can therefore use sensor 46 for detecting both the absence/presence of an occupant on support deck 30, as well as the absence/presence of a person in head end area 90. The location of thermal sensor 46 can be varied from that shown in FIG. 8, including the addition of one or more additional thermal sensors 46.

After detecting the presence of a person within the vicinity of control input 132 (i.e. within the head end area 90 of the illustrated embodiment), controller 60 moves from step 130 to step 134 where it sends a signal to main controller 74 instructing it to enable control input 132. This enable instruction causes main controller 74 to activate or allow the use of control input 132 for controlling the propulsion system. In other words, in the absence of the enable signal, any manipulation of control input 132 by a user that would otherwise cause movement of the person support apparatus 20d is rendered inoperative. The propulsion system therefore does not propel any of the wheels 24 in the absence of this enable system. Once the propulsion system is enabled at step 134, however, a user will be free to manipulate control input 132 in order to propel support apparatus 20d to a new location, and such manipulations will be acted upon by main controller 74 to control motor 84 and the propulsion of support apparatus 20d.

Once the propulsion control input 132 has been enabled at step 134, controller 60 passes to step 136 where it continues to analyze the thermal images generated by thermal sensor 46 to monitor whether a person is still positioned within the vicinity of control input 132. So long as an individual is detected within this vicinity, main controller 74 will continue to enable control input 132. If, however, thermal sensor 46 detects the departure of the individual from the area of control input 132, controller 60 will send a signal to main controller 74 at step 138 instructing it to disable control input 132. This disable signal will also cause main controller 74 to terminate power to motor 84 to thereby bring any continuing motion of person support apparatus 20d to a stop. Further, main controller 74 will also activate the bed brakes 92 at a subsequent step 140. Step 140, in at least one embodiment, occurs a predetermined time period after step 138 in order to not instantaneously cause person support apparatus 20d to come to an immediate and abrupt halt. In other embodiments, brakes 92 may be applied at the same time as the propulsion system is disabled. Variations of propulsion enable algorithm 70d are, of course, possible.

Figure 9:
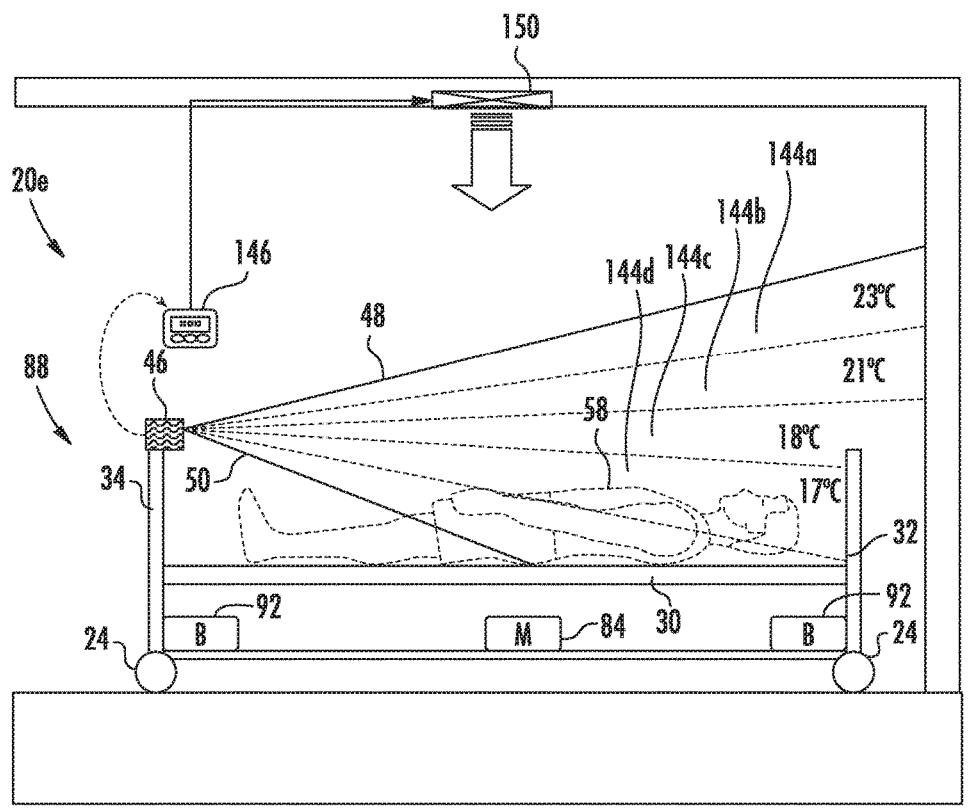
FIG. 9 is a side, elevation diagram of an embodiment of a person support apparatus incorporating an automatic micro-climate control feature.

FIG. 9 illustrates another person support apparatus 20e that is configured to carry out an automatic environmental control algorithm 70e. One embodiment of the automatic environmental control algorithm is outlined in FIG. 15. Automatic environmental control algorithm 70e is generally designed to ensure that an occupant of person support apparatus 20e is more accurately experiencing a desired temperature, as will be discussed in greater detail below.

Figure 15:
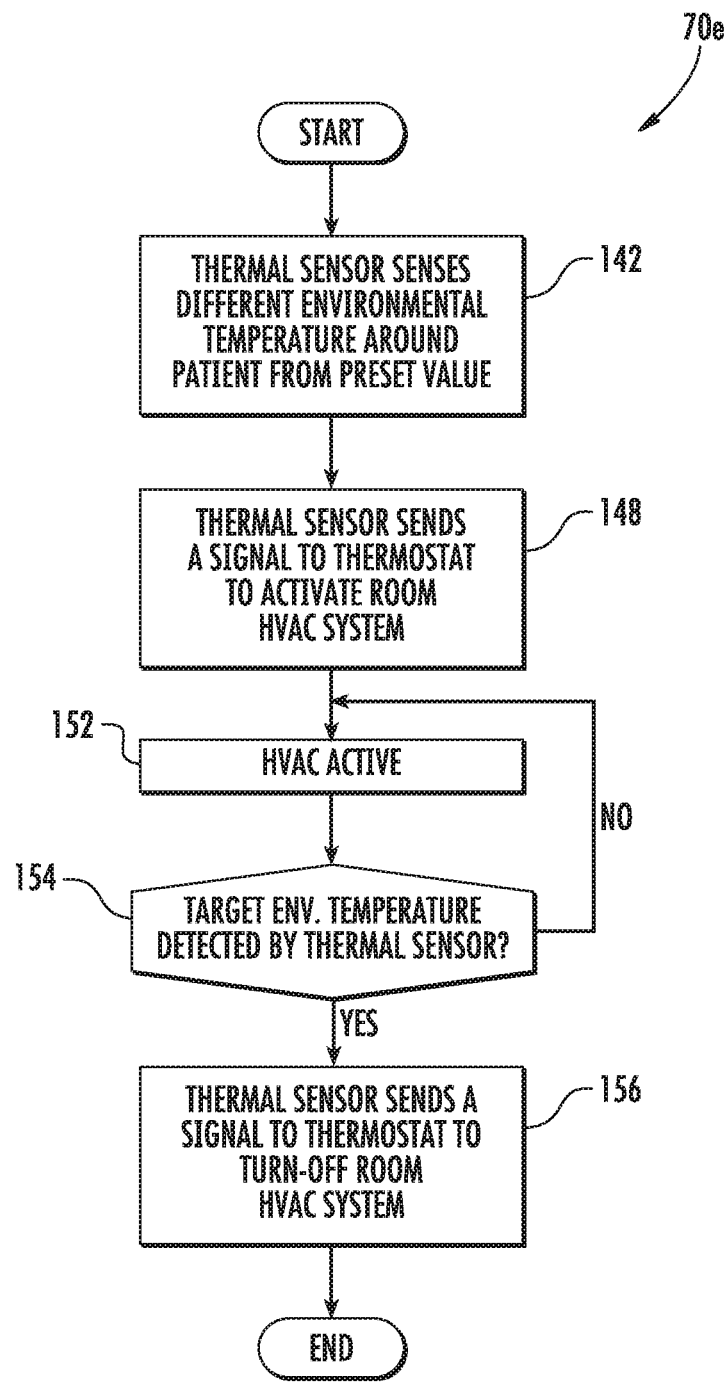
FIG. 15 is a flowchart of an illustrative algorithm carried out by the person support apparatus of FIG. 9.

With specific reference to FIG. 15, microenvironment control algorithm 70e begins at an initial step 142 where the thermal images from thermal sensor 46 (FIG. 9) are analyzed by controller 60 to determine different environmental temperatures, if any, in the area closely surrounding the occupant of person support apparatus 20e (i.e. the occupant's microenvironment). For example, as shown in FIG. 9, thermal sensor 46 detects first region 144a corresponding to 23 degrees Celsius, a second region 144b corresponding to 21 degrees Celsius, a third region 144c corresponding to 18 degrees Celsius, and a fourth region 144d corresponding to 17 degrees Celsius. The number of different regions 144 that are sensed by thermal sensor 46 can be varied from that shown in FIG. 9 and, of course, it may turn out—depending upon the current environmental conditions—that the temperatures detected in at least some of the multiple regions 144 are the same.

Regardless of the specific number of regions 144 that are analyzed, controller 60 also compares at step 142 the sensed temperature values to a desired environmental temperature value. The desired environmental temperature value may be set via a thermostat 146 positioned in the room in which person support apparatus 20e is positioned, or it may be positioned elsewhere. In another variation, the desired environmental temperature value may be set via one or more controls positioned on person support apparatus 20e. In either case, controller 60 compares this desired environmental temperature value to the temperature value detected within the immediate, or near immediate, vicinity of occupant 58. Thus, in the example shown in FIG. 9, controller 60 compares the desired environmental temperature value to the temperature value corresponding to either third region 144c (18° C.) or fourth region 144d (17° C.), depending upon how person support apparatus 20e is configured. If the value of the desired environmental temperature value differs from the measured temperature (of region 144c or 144d), controller 60 moves to step 148.

At step 148 (FIG. 15), controller 60 sends a message to thermostat 146, or any other structure that is capable of controlling a Heating, Ventilating, and Air Conditioning (HVAC) system 150. The control message sent in step 148 instructs the HVAC system 150 to direct more heat to the room of occupant 58 if the temperature value measured via thermal sensor 46 was below the desired environmental temperature value, or to direct cooler air to the room of the occupant 58 if the temperature value measured via thermal sensor 46 was above the desired environmental temperature value. At step 152, HVAC system 150 responds to the message sent at step 148 and outputs the corresponding warm or cool air. At step 154, controller 60 re-checks the temperature values sensed by sensor 46 in the vicinity of occupant 58 (e.g. within region 144c or 144d) and again compares the sensed temperature value to the desired environmental temperature value. If a difference still remains between the two values, control passes back to step 152 where HVAC system 150 continues to output the warm or cool air. From there, control passes onto step 154 where another check of the temperature values sensed by sensor 46 within the vicinity of the occupant 58 is made. To the extent this temperature continues to differ from the desired environmental temperature value, steps 152 and 154 continue to cycle.

Eventually, control will pass to step 156 when the temperature within the close vicinity of the occupant 58 is equal to the desired environmental temperature value. When this happens, controller 60 will send a signal at step 156 to shut off the HVAC system so that no more warm or cool air is delivered to the occupant of person support apparatus 20e. After a predetermined amount of time, or any other suitable trigger, microenvironment control algorithm 70e will begin again at step 142. Microenvironment control algorithm 70e will therefore ensure that the immediately surround environment of the occupant 58 is maintained at a desired temperature. This improves the accuracy of a conventional HVAC system where the temperature of a room or area is controlled based upon the temperature measured at the location of thermostat 146. However, because thermostat 146 may be positioned in a different location or at a different height than occupant 58, the temperature within the immediate vicinity of occupant 58 may differ from the temperature sensed at thermostat 146 and thermostat 146 will not correct this discrepancy. In other words, a conventional HVAC system will typically control only the microenvironment of the thermostat with precision, not the microenvironment of a different location. Microenvironment control algorithm 70e, however, ensures that the microenvironment of an occupant 58 of support deck 30 is controlled precisely, rather than that of the thermostat 146.

Figure 10:
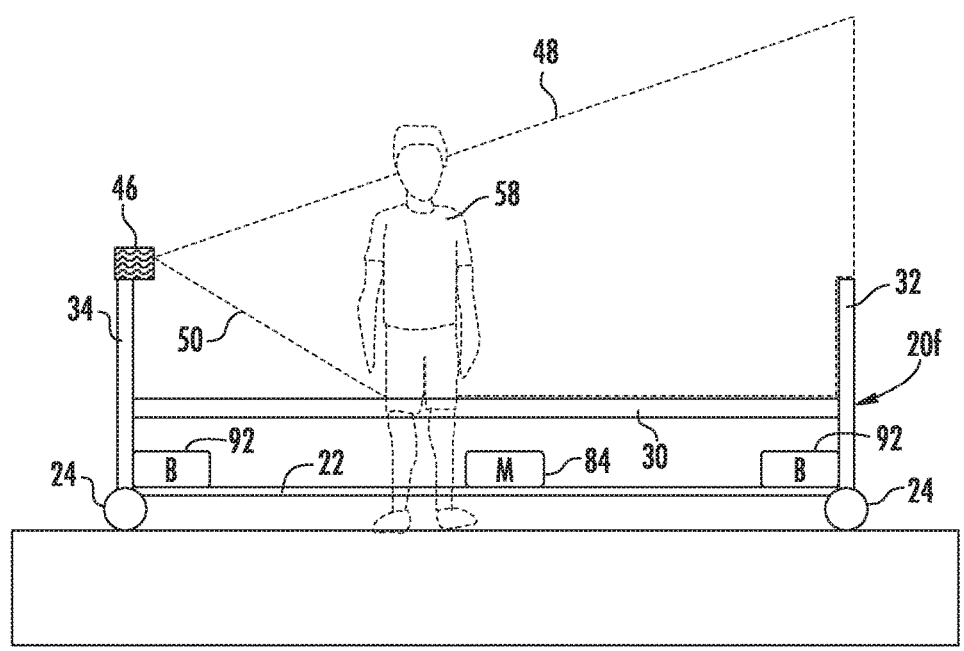
FIG. 10 is a side, elevation diagram of an embodiment of a person support apparatus incorporating an automatic arming feature of an exit detection system.

FIG. 10 illustrates another person support apparatus 20f that is configured to carry out an exit detection system automatic arming algorithm 70f. A first embodiment of the exit detection system automatic arming algorithm 70f is outlined in FIG. 16. Exit detection system automatic arming algorithm 70f is generally designed to ensure that exit detection system 83 is automatically armed whenever a person or patient 58 is occupying person support apparatus 20, unless a caregiver has taken one or more affirmative steps to indicate that that particular person 58 is not at risk for falls, and therefore can be allowed to occupy person support apparatus 20 without the exit detection system 83 being armed. This automatic arming of exit detection system 83 helps ensure that caregivers do not inadvertently forget to arm exit detection system 83, thereby leading to a potential increased risk of a patient falling and injuring himself or herself.

The steps of algorithm 70f are carried out by controllers 60 and 74. The particular controller which carries out a particular step can vary. In some embodiments, only a single controller is used that combines all of the functionality of controllers 60 and 74 into a single controller. In still other embodiments, more than two controllers are used. It will be understood that any references below to a specific controller executing a particular step of algorithm 70f are merely provided for purposes of illustrating one illustrative embodiment, and that algorithm 70*f* can be varied so as to have that particular step carried out by a different controller.

Figure 16:
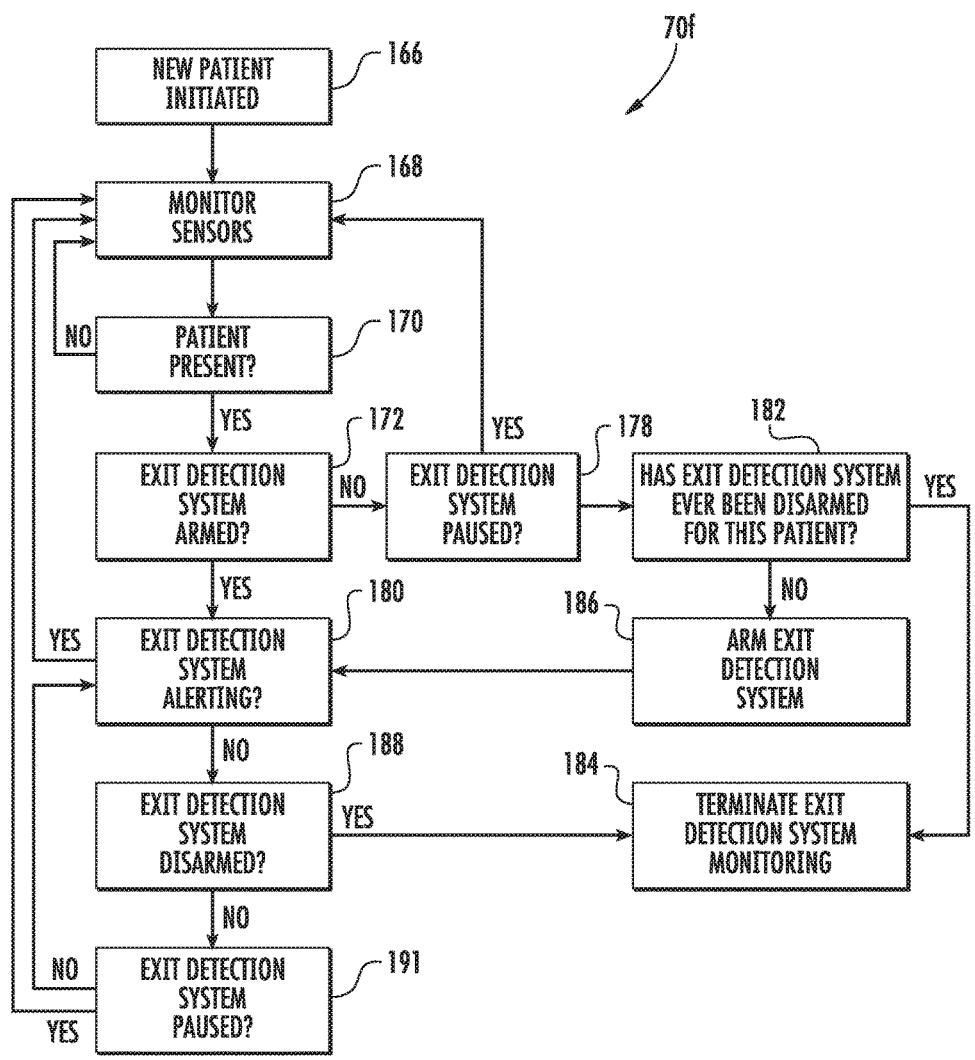
FIG. 16 is a flowchart of an illustrative algorithm carried out by the person support apparatus of FIG. 10.
Figure 17:
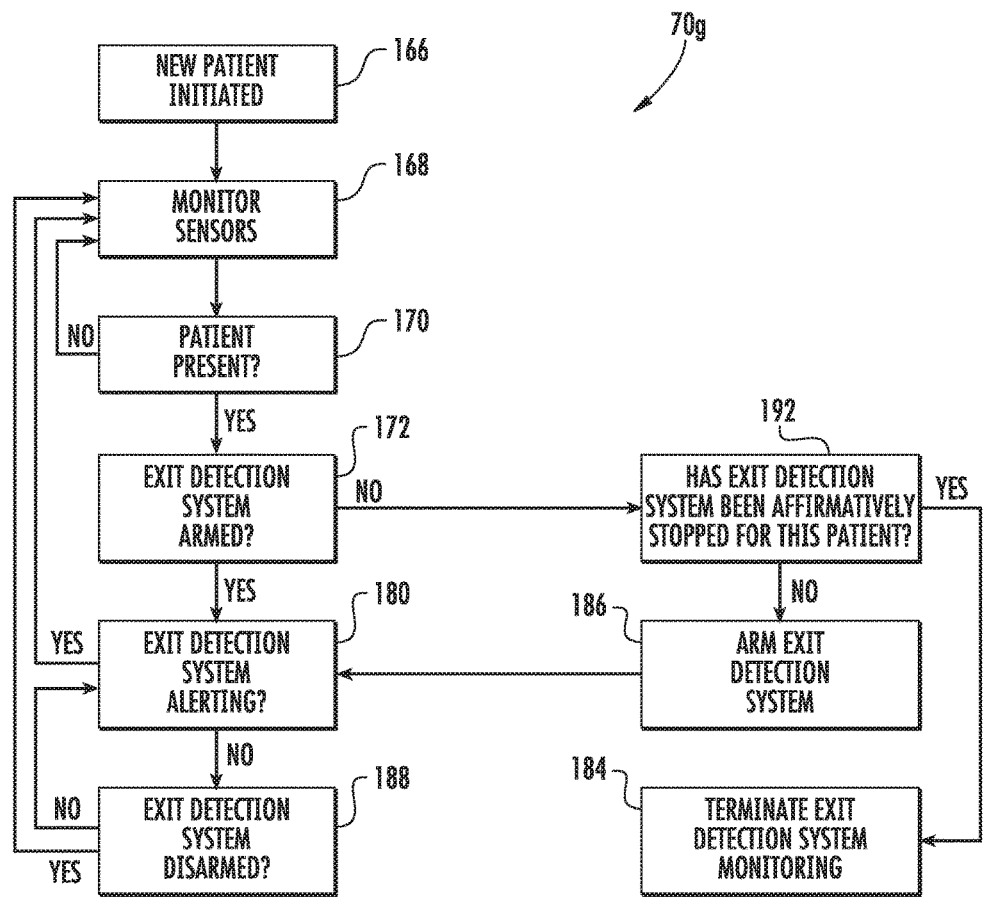
FIG. 17 is a flowchart of an alternative algorithm carried out by the person support apparatus of FIG. 10.

With specific reference to FIG. 16, exit detection system automatic arming algorithm 70*f* begins when a new patient button 164 (FIG. 4) is pressed at step 166. In the embodiment of FIG. 4, new patient button 164 is included as part of one of the control panels 82 on person support apparatus 20. New patient button 164, which may be physically implemented as a button or which may be physically implemented in other manners (e.g. a switch, an icon on a touchscreen, a lever, etc.), is activated by a caregiver when a new patient is assigned to a particular person support apparatus 20. In addition to starting algorithm 70*f*, the pressing of new patient button 164 may perform additional tasks, such as clearing from a memory on-board person support apparatus 20 any data that was previously saved for a previous patient (e.g. the previous patient's weight, treatment history, fall risk, etc.).

After new patient button 164 is pressed at step 166, algorithm 70*f* begins monitoring the outputs from the one or more sensors 46 at step 168 (FIG. 16). At step 170, algorithm 70*f* analyzes the thermal images generated by sensors 46 during step 168 to determine whether or not a patient is present on patient support apparatus 20. If controller 60 determines that no patient is present, control returns back to step 168 where continued monitoring and analysis of the outputs from sensors 46 occurs in a loop fashion via steps 168 and 170 until an occupant of patient support apparatus 20 is detected.

If/when a patient is detected on patient support apparatus 20 at step 170, control moves to step 172 where controller 74 checks to see if exit detection system 83 has been armed or not. The arming of exit detection system 83 refers to activating the exit detection system 83 such that it issues an alarm when the patient exits from person support apparatus 20. The disarming of exit detection system 83 refers deactivating exit detection system 83 such that the patient may freely exit person support apparatus 20 without an alarm being generated. As shown in the example of FIG. 4, the arming and disarming of exit detection system 83 may be carried out, respectively, by an arm button 174 and a disarm 176 positioned on one or more of the control panels 82. In some embodiments, buttons 174 and 176 are combined into a single button that toggles between arming and disarming exit detection system 83 when it is repeatedly pressed. As with new patient button 164, buttons 174 and 176 (and button 190 discussed below) may alternatively be physically implemented in other manners (e.g. as switches, icons on a touchscreen, levers, etc.)

After step 172, control proceeds to either step 178 if exit detection system 83 is not armed, or to step 180 if exit detection system 83 is armed. When exit detection system 83 is not armed and control proceeds to step 178, controller 74 checks to see if exit detection system 83 has been paused by a user. The pausing of exit detection system 83 is carried out by a user pressing on pause button 190 on control panel 82 (FIG. 4). When exit detection system 83 is paused, the patient is free to exit from person support apparatus 20 without triggering an exit alert. However, unlike when exit detection system 83 is disarmed, when exit detection system 83 is paused, exit detection system 83 will automatically reactivate itself after the return of the patient to person support apparatus 20. That is, after the patient returns, exit detection system 83 resumes issuing exit alerts if/when it detects the departure of the patient from patient support apparatus 20.

If controller 74 determines at step 178 that the pause button has been pressed, control returns back to step 168 where sensors 46 are repetitively monitored until the patient's presence is detected on board person support apparatus 20. Once detected, control proceeds in the manner previously described. If controller 74 determines at step 178 that the pause button has not been pressed, control passes to step 182. At step 182, controller 74 determines whether exit detection system 83 has ever been previously disarmed for the particular patient on board person support apparatus 20. In one embodiment, this is determined by setting a flag in memory when disarm button 176 is first pressed for a particular patient and consulting this flag. (This flag is automatically reset when new patient button 164 is pressed). The purpose of step 182 is to allow a caregiver to shut off and/or override the automatic arming of exit detection system 83 when the caregiver has determined that the patient is not a fall risk and that exit alerting is not needed for that particular patient. This is accomplished by the caregiver taking the affirmative step of pressing disarm button 176. Once disarmed for a particular patient, the exit detection system is never automatically re-armed by algorithm 70*f* until a new patient is assigned to that particular patient support apparatus 20. Algorithm 70*f* thereby automatically arms exit detection system 83 for all patients and continues to automatically re-arm it after a patient exits unless the caregiver takes the affirmative step of terminating algorithm 70*f*. The result of algorithm 70*f* is that all patients are presumed to be a fall risk, and are thus all automatically monitored for exit detection, unless a caregiver takes an affirmative step to stop the automatic arming of exit detection system 83.

If controller 74 determines at step 182 that exit detection system 83 was previously disarmed for this particular patient, control passes to step 184, where algorithm 70*f* terminates, and no further automatic arming of exit detection system 83 is carried out by algorithm 70*f* until new patient button 164 is pressed. If controller 74 determines at step 182 that exit detection system 83 was not previously disarmed for this particular patient, control passes to step 186, where controller 74 automatically arms exit detection system 83. After automatically arming exit detection system 83 at step 186, control passes to step 180.

As shown in FIG. 16, step 180 is reached either via step 172 (when exit detection system 83 is manually armed) or via step 186 (when exit detection system 83 is automatically armed by controller 74. Regardless of the route by which step 180 is reached, controller 74 determines at step 180 whether or not exit detection system 83 is issuing an alert or not (i.e. whether the patient has exited, or otherwise moved in a manner that triggered exit detection system 83). If exit detection system 83 is issuing an alert, control proceeds back to step 168, where algorithm 70*f* awaits the return of the patient to patient support apparatus 20. If exit detection system 83 is not issuing an alert, controller 74 proceeds to step 188, where it determines whether or not exit detection system 83 has been disarmed or not. If system 83 has been disarmed, algorithm 70*f* terminates at step 184 until new patient button 164 is pressed again. If system 83 has not been disarmed, controller 74 proceeds to step 191, where it determines whether exit detection system 83 has been paused or not. If it has, control returns to step 168. If it has not, control returns to step 180.

From the foregoing description of the steps of algorithm 70*f*, it can be seen that algorithm 70*f* will automatically arm exit detection system 83 after a patient enters the patient support apparatus 20, unless the caregiver takes the affirmative step of disarming the exit detection system. Algorithm 70f will also automatically re-arm exit detection system 83 after exit detection system 83 has been paused. This re-arming, in at least one embodiment, enables the pause button 190 to pause exit detection system 83 until a predefined event occurs (patient re-entry into person support apparatus 20), rather than a predefined threshold amount of time passes. In this manner, if pause button 190 is pressed to allow a patient to leave person support apparatus 20 for treatment, to use the restroom, or for other purposes, there is no set time limit by which the patient must return to person support apparatus 20 in order to avoid exit detection system 83 automatically re-arming itself, detecting no patient presence, and issuing an alert. Algorithm 70f therefore allows exit detection system 83 to be paused for an indefinite amount of time and automatically terminate the pause when the patient returns to person support apparatus 20.

FIG. 17 illustrates an alternative exit detection system automatic arming algorithm 70g. Those steps of algorithm 70g that are the same as ones found in algorithm 70f bear the same reference numbers and not described further herein. In general, algorithm 70g differs from algorithm 70f in that it is adapted to operate on a person support apparatus 20 that does not include any pause button 190, or other means of pausing exit detection system 83 (other than disarming exit detection system 83). More specifically, algorithm 70g differs from algorithm 70f in that it omits steps 178 and 188 (both of which relate to pausing exit detection system 83), and it includes a modified step 192 that replaces step 182 of algorithm 70f. At step 192, controller 74 determines whether or not a caregiver has taken an affirmative step to indicate that the current patient associated with person support apparatus 20 is not a fall risk, and therefore does not need to have exit detection system 83 armed while the patient is in person support apparatus 20. The affirmative step can take on a wide variety of forms but, unlike algorithm 70f, it does not include pressing disarm button 176, which is used to stop exit detection monitoring when the patient leaves person support apparatus 20 in the presence of a caregiver. In other words, unlike algorithm 70f, the pressing of disarm button in algorithm 70g does not automatically terminate algorithm 70g. Instead, terminating the auto-arming function of algorithm 70g is accomplished by some other affirmative act. In some embodiments, this affirmative act includes entering one or more scores from a fall risk assessment performed by healthcare personnel into controller 74 (via one or more control panels 82). In other embodiments, other affirmative acts can be used.

Algorithm 70g also differs from algorithm 70f in that controller 74 proceeds back to step 168 from step 188 if controller 74 detects that exit detection system 83 has been disarmed. The result of this returning to step 168 is that algorithm 70g will automatically re-arm exit detection system 83 after it has been disarmed when the patient returns to patient support apparatus 20 (unless the affirmative act of terminating algorithm 70g has been performed).

In addition to the algorithms 70a-g that have been described above, controller 60 may alternatively or additionally be programmed to carry out an exit alert algorithm. Such an exit alert algorithm issues an alert when an occupant 58 of a person support apparatus, such as, but not limited to person support apparatus 20, exits from support deck 30. The alert may be an audio, visual, and/or audiovisual alert that is local to the person support apparatus, and/or it may be a remote alert that is issued at one or more remote locations (e.g. a nurses' station within a medical facility). Controller 60 carries out such an exit alert algorithm by analyzing the thermal images from one or more thermal sensors 46 that are positioned to have a thermal field of view that encompasses support deck 30. If the analysis of those thermal images indicates that a person is occupying support deck 30, no alert is issued. If the analysis of those thermal images indicates that a person has departed support deck 30, then an alert is issued.

The exit alert algorithm may be modified or supplemented to also issue one or more alerts prior to the complete departure of an occupant from the person support apparatus. In other words, the exit alert algorithm may be modified to include issuing both an exit alert and/or one or more pre-exit alerts. Such pre-exit alerts are based upon analyzing the thermal images from sensor 46 to determine whether the occupant is moving in a way suggestive of a likely future exit. Such movement includes moving toward either of the sides of support deck 30, flipping up a side rail 44 of the support apparatus, sitting up, moving toward one end of support deck 30, or making other movements that indicate likely departure in the near future.

In some embodiments, when controller 60 is modified to carry out an exit alert algorithm, the components of person support apparatus 20 that are shown in FIG. 4 are modified to remove the exit detection system 83. This is because the function of the exit detection system 83—when controller 60 is modified—is being carried out by controller 60 and sensors 46. The use of both exit detection system 83 and sensors 46 for determining when a person exits support apparatus 20 is not necessary, and so exit detection system 83 as a separate stand-alone system is eliminated. It is replaced by sensors 46 and controller 60. Thus, for example, when person support apparatus 20 uses sensors 46 for detecting a patient's exit, for example, algorithms 70f and 70g continue to perform the steps shown in FIGS. 16 and 17, however, the steps that reference the exit detection system 83 refer to sensors 46 and/or controller 60, rather than a system separate from sensors 46 and controller 60.

In still other embodiments, when controller 60 is modified to carry out an exit alert algorithm, exit detection system 83 is retained on person support apparatus 20. In these embodiments, the information gathered from sensors 46 and from exit detection system 83 are combined together and used in combination to determine whether or not an exit alert should be issued. This combination of exit detection sensors may create a more robust system for detecting a person's departure and/or provide additional levels of alerting, if desired. For example, the use of sensors 46 and controller 60 to determine a person's impending departure may allow for an alert to be issued sooner in the process of the person's departure than may be possible using exit detection system 83. As an example, if exit detection system 83 is a load cell based system (e.g. the system disclosed in commonly assigned U.S. Pat. No. 5,276,432 issued to Travis), sensors 46 may be able to detect movement of the person on support apparatus 20 that is indicative of an impending departure—and that triggers an exit alert—prior to the detection of an exit alert condition via the load cells.

In all of the algorithms that have been described above, controller 60 includes information indicating where the one or more thermal sensors 46 are mounted in relation to the corresponding support apparatus 20, as well as the angular relationship of the sensor 46's field of view with respect to the support apparatus 20 (and/or any other sensors 46 that are present). Controller 60 uses this information to determine how the different thermal pixels within the thermal images 54 correlate to different physical locations, both on the patient support apparatus and off. Using this information, controller 60 does not need to rely on any predefined thermal or visual markers in order to correlate thermal sensor 46's frame of reference to the physical frame of reference of the person support apparatus. In other words, it is not necessary for the occupant 58 of person support apparatus 20, or any non-occupants of person support apparatus 20, to wear a special marker that emits a specialized heat signature, or specialized reflective signature, in order for controller 60 to determine the location of such individuals relative to person support apparatus 20, including whether or not the detected heat signature is from a person that is located near, but not on, person support apparatus 20. Instead, controller 60 is able to determine the relative location of a person, or other heat emitting entity, to person support apparatus 20 by analyzing where the heat signature appears in the thermal image 54, and using the stored information about where the thermal sensor 46 is mounted in relation to the person support apparatus, as well as it relative orientation, to correlate the heat signature to a physical location. Carrying out any of the algorithms discussed herein can therefore be accomplished without having to apply any specialized markers to any individuals, or any landmark reference locations within the room or on the person support apparatus.

In any one or more of the algorithms discussed herein, controller 60 may be further configured to correlate thermal images from multiple thermal sensors 46 in a manner that generates stereoscopic thermal images. Such stereoscopic thermal images enable controller 60 to determine the depth of a particular thermal pattern within a thermal image, in addition to the side-to-side and up-and-down position of the thermal pattern. Controller 60 determines this depth information by utilizing stored data that indicates the spatial and angular relationships of the two or more thermal sensors 46 that generate thermal images for processing by controller 60. That is, controller 60 stores information indicating a distance between the multiple thermal sensors 46, the angular orientations of sensors 46 with respect to each other, and information sufficient to correlate these parameters to a frame of reference in which the position and orientation of person support apparatus 20 is known. Determining the depth of objects detected by sensors 46 may be carried out in one or more conventional manners, as would be known to a person of ordinary skill in the art.

In any of the above described person support apparatuses, the triggers for carrying out the various algorithms described herein can be a manual trigger. In other words, in any of the above embodiments, person support apparatus may be modified to include a control on one or more of its control panels 82 that allows a user to selectively activate or deactivate any of algorithms 70*a-g* and/or the exit alert algorithm. This enables a person, such as a caregiver in a healthcare setting, to decide which functions will be carried out by controller 60 at any given time.

In still another embodiment, thermal sensors 46 may be provided on the person support apparatus, but none of the software necessary for carrying out the algorithms is initially present on the person support apparatus. Instead, the person support apparatus is configured to download the appropriate software from a computer network connection in any of the manners described in commonly-assigned co-pending U.S. patent application Ser. No. 14/211,613 filed Mar. 14, 2014 by inventors Michael Hayes et al. and entitled PATIENT SUPPORT APPARATUS WITH REMOTE COMMUNICATIONS, the complete disclosure of which is hereby incorporated by reference. In yet another alternative embodiment, instead of completely downloading the software necessary for carrying out one or more of these algorithms, the person support apparatus may be configured to access a network service that carries out, either partially or wholly, these algorithms in a manner where the person support apparatus acts as a thin client with respect to the network service. Such use of network services by a person support apparatus is described in more detail in the Ser. No. 14/211,613 patent application mentioned above, and any of those methods may be incorporated into any of the person support apparatuses described herein to execute the algorithms discussed herein.

In addition to carrying out the various algorithms described herein, the outputs of thermal sensors 46 can be fused with other sensor data to provide improved reliability, additional information, and/or enhanced sensing abilities. For example, if the person support apparatus includes multiple load cells for detecting a person's weight, for monitoring the person's movement, or for issuing an exit or pre-exit alert in appropriate situations, the weight information from the load cells can be combined with the thermal image data generated from the thermal sensor 46 in order to improve, augment, or enhance the functions provided by the load cells and/or thermal sensors 46. As one example, the thermal image sensors 46 can be used to detect if someone places an additional object onto support deck 30, or removes an object therefrom. This information can be forwarded to the main controller 74 so that the tare weight associated with the load cell-based scale system can be appropriately adjusted. This can reduce or avoid the necessity of a caregiver having to manually re-tare the scale system.

As another example, the thermal image data from sensors 46 can also be fused with one or more other sensors that are used by main controller 74 of the person support apparatus to determine the sleep status of an occupant of the person support apparatus. For example, commonly-assigned co-pending U.S. patent application Ser. No. 14/212,367 entitled PATIENT SUPPORT APPARATUS WITH PATIENT INFORMATION SENSORS (inventors Michael Hayes et al.) discloses multiple person support apparatuses that have sensors for determining the sleep status of an occupant of the person support apparatus. Such sensors include, but are not limited to, vital sign sensors for sensing the occupant's heart rate and/or breathing rate. The data from these sensors can be fused with the data from thermal sensors 46 to more accurately determine the sleep state of the occupant. For example, the fact that a person is even present on support deck 30 can be detected and/or verified by the heat pattern of the individual within the thermal field of view of one or more sensors 46. Further, that the occupant is asleep can be detected and/or verified by the relative lack of movement of the person via analysis of the thermal images generated by the thermal sensors 46. Still further, the position and/or orientation of the individual can be detected by analysis of the thermal images and this data can be factored into the determination of whether a person is asleep or not. The data from thermal sensors 46 can also be fused with data from still other sensors, as would be understood by one skilled in the art.

Figure 18:
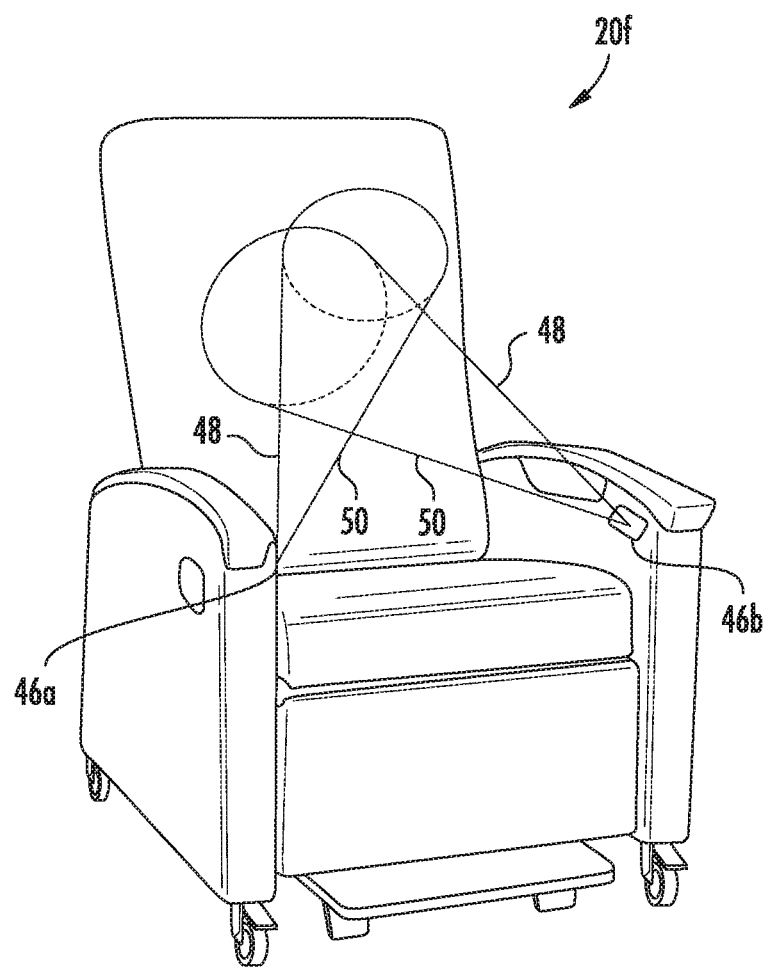
FIG. 18 is a perspective view of another embodiment of a person support apparatus that may incorporate any one or more of the features described herein.

FIG. 18 illustrates another embodiment of a person support apparatus 20*f*. Person support apparatus 20*f* of FIG. 18 is a recliner that includes two thermal sensors 46*a* and 46*b* having fields of view that are configured to detect thermal data in the torso region of an individual who is seated in person support apparatus 20*f*. Person support apparatus 20*f* includes a controller 60 that may be configured to carry out any of the algorithms described herein. Further, person support apparatus 20*f* may include any one or more of the features described in commonly-assigned co-pending U.S.

patent application Ser. No. 14/212,009 filed Mar. 14, 2014 and entitled MEDICAL SUPPORT APPARATUS (inventors Christopher Hough et al.), the complete disclosure of which is hereby incorporated herein by reference.

In still another embodiment, a sensor comprising a near infrared emitter and detector is used to detect the presence of fluids on the floor within the vicinity of a person support apparatus, such as, but not limited to, any of the person support apparatuses 20, 20*a*, 20*b*, 20*c*, 20*d*, or 20*e* described herein. The emitter portion of the sensor is adapted to output electromagnetic waves generally in the 900 nm region. Such waves are highly absorbed by water. As a result, when the emitter outputs waves in this region toward the floor, the reflected intensity of those waves, as detected by the detector portion of the sensor, will be reduced if fluids, such as water or urine, are present as compared to when no such fluids are present. The analysis of the reflected waves is carried out by controller 60. Controller 60 issues an alert if fluid is detected. The alert may be local, remote, or a combination of the two.

When the sensor used to detect the presence or absence of fluids is incorporated into one of the person support apparatuses described herein, the detector portion of the sensor used to detect fluids can be integrated into one of the thermal sensors 46. In other words, one or more of the thermal sensors 46 can be used to detect the presence or absence of floor fluids in addition to the other item(s) that are detected by the thermal sensor 46, as set forth in the algorithms described above. Alternatively, the fluid detector portion can be a device that is separate from the one or more thermal sensors 46.

In still another embodiment, a thermal sensing sheet (not shown) having a matrix of thermal sensors is used to generate thermal maps or images of persons and/or objects positioned on the person support apparatus (which can be, but is not limited to, any of person support apparatuses 20, 20*a*, 20*b*, 20*c*, 20*d*, 20*e*). The thermal sensing sheet is integrated into a mattress cover that fits over a mattress positioned on top of support deck 30, in one embodiment. In another embodiment, the thermal sensing sheet is included in a layer that is separate from the mattress cover. In still another embodiment, the thermal sensing sheet is incorporated into the mattress itself. The thermal sensing sheet includes an array or matrix of thermal sensors that are each capable of sensing temperature. The sensed temperature will generally be affected by the presence or absence of a person, or other object, positioned on top of the thermal sensing sheet. Controller 60 is adapted to analyze the thermal map generated by the thermal sensing sheet and to use it to determine the absence or presence of a person and/or object, the position of the person and/or object on the person support apparatus, movement of the person, orientation of the person (e.g. lying on side or back; sitting up, etc.); and/or other characteristics. This data may be fused with the thermal sensor data from thermal sensor(s) 46 and/or with any other data derived from one or more other types of sensors that may be present on the person support apparatus.

In still other embodiments, the one or more thermal sensors 46 are integrated into a transportation vehicle to count and/or track the movement of individuals in the transportation vehicle. The transportation vehicle may be a subway car, passenger railroad, bus, airplane, or the like. The thermal sensors 46 are placed at one or more strategic locations within the transportation vehicle so that thermal maps of the areas where passengers may be located are generated. These maps are analyzed to count the number of individuals, as well as to track the movement of the individuals. In yet another embodiment, the thermals sensors 46 are positioned in a movie theater showing room and used to count the number of individuals that are watching a movie. Still other applications are possible.

In still other embodiments, thermal sensors 46 may be replaced or supplemented with one or more radio frequency sensors, sonar sensors, or other types of sensors.

Various other alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
   a support surface adapted to support a person thereon;
   a thermal sensor adapted to detect a presence of a caregiver positioned adjacent a propulsion control of the person support apparatus; and
   a controller adapted to automatically carry out the following functions: (1) enable the propulsion control in response to detecting the presence of the caregiver adjacent the propulsion control, wherein the propulsion control drives a motor adapted to propel the person support apparatus when the propulsion control is enabled and activated by the caregiver; and (2) disable the propulsion control when the presence of the caregiver is not detected adjacent the propulsion control, wherein the propulsion control does not drive the motor when the propulsion control is activated by the caregiver but disabled.

2. The person support apparatus of claim 1 wherein the controller is further adapted to automatically illuminate a display screen on the person support apparatus when the presence of the caregiver is detected adjacent the propulsion control.

3. The person support apparatus of claim 2 further comprising an ambient light sensor in communication with the controller, wherein the controller changes an illumination intensity of the display screen based upon a signal from the ambient light sensor.

4. The person support apparatus of claim 1 wherein the controller is further adapted to automatically activate a brake if the caregiver is no longer positioned adjacent the propulsion control and has not manually activated the brake.

5. The person support apparatus of claim 1 wherein the thermal sensor is further adapted to sense the person when the person is positioned on the support surface and the thermal sensor is part of an occupant detection system adapted to issue an alert if the person exits the support surface.

6. A person support apparatus comprising:
   a support surface adapted to support a person thereon;

an occupancy detection system adapted to detect whether a person is present on the support surface or not, a thermal sensor adapted to detect thermal radiation emitted from within a field of view, the field of view including a floor on which the person support apparatus is supported; and a controller adapted to process outputs from the thermal sensor to detect a heat pattern corresponding to the person and to use the heat pattern to track movement of the person off of the support surface and to determine if the person moves lower than a threshold height relative to the floor, the controller further adapted to issue a fall alert if at least both of the following are true: (a) the person remains lower than the threshold height for more than a minimum amount of time, and (b) the occupancy detection system detects an absence of the person on the support surface.

7. The person support apparatus of claim 6 further comprising an infrared emitter adapted to emit infrared light onto the floor, and an infrared light sensor adapted to detect infrared light emitted by the infrared emitter and reflected back to an infrared sensor, the controller further adapted to determine if a fluid is present on the floor based upon a difference in an intensity of the infrared light reflected from the fluid and an intensity of the infrared light reflected from the floor.

8. The person support apparatus of claim 7 wherein the controller is further adapted to issue an alert in response to detecting fluid on the floor.

9. The person support apparatus of claim 6 wherein the occupancy detection system comprises a second thermal sensor adapted to detect thermal radiation emitted from a field of view that includes the support surface.

10. The person support apparatus of claim 9 wherein the controller activates the thermal sensor after determining that the person is present on the support surface.

11. The person support apparatus of claim 6 wherein the occupancy detection system comprises a plurality of load cells.

12. The person support apparatus of claim 6 further comprising a second thermal sensor having a second field of view that overlaps with the field of view of the thermal sensor, the controller further adapted to use outputs from the thermal sensor and second thermal sensor to generate a stereoscopic thermal image and to use the stereoscopic thermal image to determine if the heat pattern falls below the threshold height.

13. A person support apparatus comprising:
a support surface adapted to support a person thereon;
a thermal image sensor adapted to capture thermal images of a region adjacent the support surface that includes ambient air; and
a controller adapted to process the thermal images to determine a temperature of the ambient air in the region and to compare the temperature of the ambient air to a desired temperature value.

14. The person support apparatus of claim 13 wherein the controller is further adapted to send a message to an environmental controller if the temperature of the ambient air differs from the desired temperature value.

15. The person support apparatus of claim 14 wherein the controller is further adapted to send another message to the environmental controller when the temperature of the ambient air in the region reaches the desired temperature value.

16. The person support apparatus of claim 14 wherein the controller is further adapted to process the thermal images to determine when the person enters the support surface.

17. The person support apparatus of claim 16 wherein the controller is further adapted to automatically arm an exit detection system when the person enters the support surface.

18. The person support apparatus of claim 13 further comprising a footboard, and wherein the thermal image sensor is positioned on the footboard.

* * * * *